United States Patent
Long et al.

(10) Patent No.: US 9,956,406 B2
(45) Date of Patent: May 1, 2018

(54) STIMULATION MANAGEMENT

(71) Applicant: Cochlear Limited, Macquarie University, NSW (AU)

(72) Inventors: Christopher Joseph Long, Centennial, CO (US); Joerg Pesch, Mechelen (BE); Zachary Mark Smith, Greenwood Village, CO (US)

(73) Assignee: COCHLEAR LIMITED, Macquarie University, NSW (AU)

( * ) Notice: Subject to any disclaimer, the term of this patent is extended or adjusted under 35 U.S.C. 154(b) by 273 days.

(21) Appl. No.: 14/547,862

(22) Filed: Nov. 19, 2014

(65) Prior Publication Data

US 2015/0258337 A1 Sep. 17, 2015

Related U.S. Application Data

(60) Provisional application No. 61/952,517, filed on Mar. 13, 2014.

(51) Int. Cl.
*A61N 1/36* (2006.01)
*A61N 1/05* (2006.01)

(52) U.S. Cl.
CPC ..... *A61N 1/36032* (2013.01); *A61N 1/36036* (2017.08); *A61N 1/0541* (2013.01)

(58) Field of Classification Search
CPC ... A61B 5/7203; A61B 5/7207; A61B 5/7217; A61N 1/0541; A61N 1/36032
See application file for complete search history.

(56) References Cited

U.S. PATENT DOCUMENTS

| 5,139,028 | A | * | 8/1992 | Steinhaus | A61B 5/0006 600/508 |
|---|---|---|---|---|---|
| 6,157,861 | A | | 12/2000 | Faltys et al. | |
| 7,110,821 | B1 | | 9/2006 | Ross | |
| 7,283,877 | B1 | | 10/2007 | Litvak et al. | |
| 7,860,573 | B2 | | 12/2010 | van den Honert | |

(Continued)

FOREIGN PATENT DOCUMENTS

EP   2165648 A1   3/2010

OTHER PUBLICATIONS

W.M.C. Klop et al., A new method for dealing with the stimulus artefact in electrically evoked compound action potential measurements, Acta Oto-laryngologica, 2004, vol. 124, pp. 137-143, Department of Otorhinolaryngology, Leiden University Medical Centre, Leiden, the Netherlands.

(Continued)

*Primary Examiner* — Michael Carey
*Assistant Examiner* — Natasha Patel
(74) *Attorney, Agent, or Firm* — Hauptman Ham, LLP; Martin J. Cosenza

(57) ABSTRACT

A method including reducing a stimulation artifact of an implantable stimulator including a plurality of stimulating electrodes by obtaining respective information on respective artifact voltages at a first location resulting from stimulation by one electrode group or respective electrode groups of the implanted stimulator and determining an adjustment regime based on the obtained information that results in a reduction of the stimulation artifact at the first location relative to that which would be the case in the absence of the regime.

25 Claims, 27 Drawing Sheets

(56) References Cited

U.S. PATENT DOCUMENTS

| | | | |
|---|---|---|---|
| 2006/0247735 A1* | 11/2006 | Honert | H04R 25/606 607/57 |
| 2007/0244410 A1 | 10/2007 | Fridman et al. | |
| 2011/0082521 A1 | 4/2011 | Botros et al. | |
| 2012/0046714 A1 | 2/2012 | Parker et al. | |
| 2012/0245655 A1 | 9/2012 | Spitzer et al. | |
| 2013/0303937 A1 | 11/2013 | van den Honert et al. | |

OTHER PUBLICATIONS

International Search Report and Written Opinion for PCT/IB2015/051864, dated Jun. 22, 2015.
Extended European Search Report for EP Patent No. 3 117 630, dated Sep. 28, 2017.

* cited by examiner

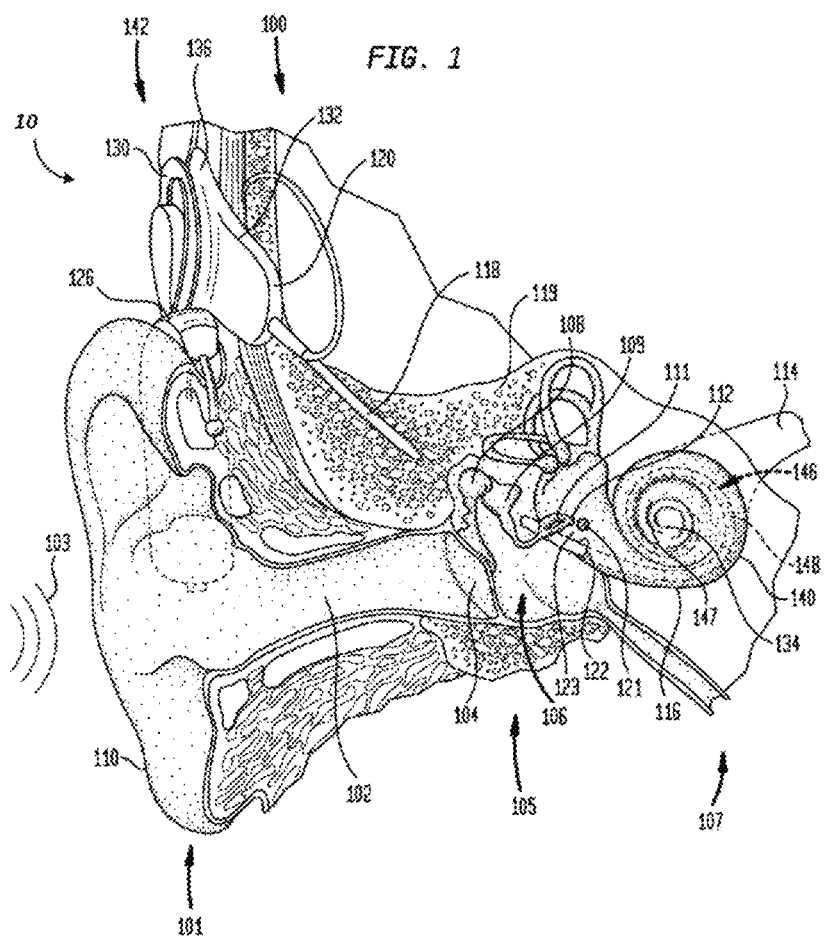

STIMULATION MANAGEMENT

This application claims priority to Provisional U.S. Patent Application No. 61/952,517, entitled STIMULATION MANAGEMENT, filed on Mar. 13, 2014, naming Christopher Joseph LONG of Centennial, Colo., as an inventor, the entire contents of that application being incorporated herein by reference in its entirety.

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. One example of a hearing prosthesis is a cochlear implant.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from hearing loss typically receive an acoustic hearing aid. Conventional hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve. Cases of conductive hearing loss typically are treated by means of bone conduction hearing aids. In contrast to conventional hearing aids, these devices use a mechanical actuator that is coupled to the skull bone to apply the amplified sound.

In contrast to hearing aids, which rely primarily on the principles of air conduction, certain types of hearing prostheses commonly referred to as cochlear implants convert a received sound into electrical stimulation. The electrical stimulation is applied to the cochlea, which results in the perception of the received sound.

SUMMARY

In accordance with an exemplary embodiment, there is a method, comprising reducing a stimulation artefact of an implanted stimulator including a plurality of stimulating electrodes by obtaining respective information on respective artefact voltages at a first location resulting from stimulation by one electrode group or respective electrode groups of the implanted stimulator, and determining an adjustment regime based on the obtained information that results in a reduction of the stimulation artefact at the first location relative to that which would be the case in the absence of the regime.

In accordance with another exemplary embodiment, there is a method, comprising supplying a first electrical current to at least a first electrode implanted in a cochlea of a recipient such that a first stimulating electrical current emanating from the first electrode stimulates the cochlea of the recipient, obtaining a property of an electrical voltage resulting from the first stimulating electrical current at at least one recording electrode that is implanted in the recipient at an intracochlear location, supplying a second electrical current to at least a second electrode implanted in the recipient cochlea such that a second stimulating electrical current emanating from the second electrode stimulates the cochlea of the recipient, obtaining a property of an electrical voltage resulting from the second electrical current at the at least one recording electrode, and determining, based on the obtained properties, at least one weighting that when at least one of the first and second electrical currents is adjusted thereby would result in a summation of the voltages of the first stimulating electrical current and the second stimulating electrical current at the at least one recording electrode to be closer to zero than that which would be the case in the absence of the weighting.

In accordance with another embodiment, there is a method, comprising recording a neural response in a cochlea resulting from stimulation from a cochlear implant, comprising (i) obtaining nullity weighting information based on artefact voltages at a first location in the cochlea for at least one current level of a plurality of respective first current levels respectively applied to respective electrodes of the cochlear implant, (ii) simultaneously stimulating the respective electrodes at respective second current levels such that a neural response is found at the first location, at least one of the second current levels being weighted by the nullity weighting information, and (iii) recording the neural response resulting from action "ii."

In accordance with yet another embodiment, there is a system comprising a control unit, and an implantable apparatus including a plurality of electrodes, wherein the implantable apparatus is configured to apply, in a controlled manner under the control of the control unit, respective first electrical currents to the respective electrodes of the plurality of electrodes such that respective stimulating electrical currents emanate from the respective electrodes of the plurality of electrodes, the system is configured to obtain respective information on respective artifact voltages at a first location resulting from the respective stimulations, and the implantable apparatus is configured to apply, subsequent to the application of the first electrical currents, in a controlled manner under the control of the control unit, respective second electrical currents to the respective electrodes of the plurality of electrodes such that respective stimulating electrical currents emanate from the respective electrodes of the plurality of electrodes and such that the stimulation artifact at the first location is substantially about zero.

BRIEF DESCRIPTION OF THE DRAWINGS

Embodiments are described below with reference to the attached drawings, in which:

FIG. 1 is a perspective view of an exemplary hearing prosthesis in which at least some of the teachings detailed herein are applicable;

FIGS. 8-10A present exemplary flowcharts for exemplary algorithms according to exemplary embodiments;

DETAILED DESCRIPTION

Figure 2A:
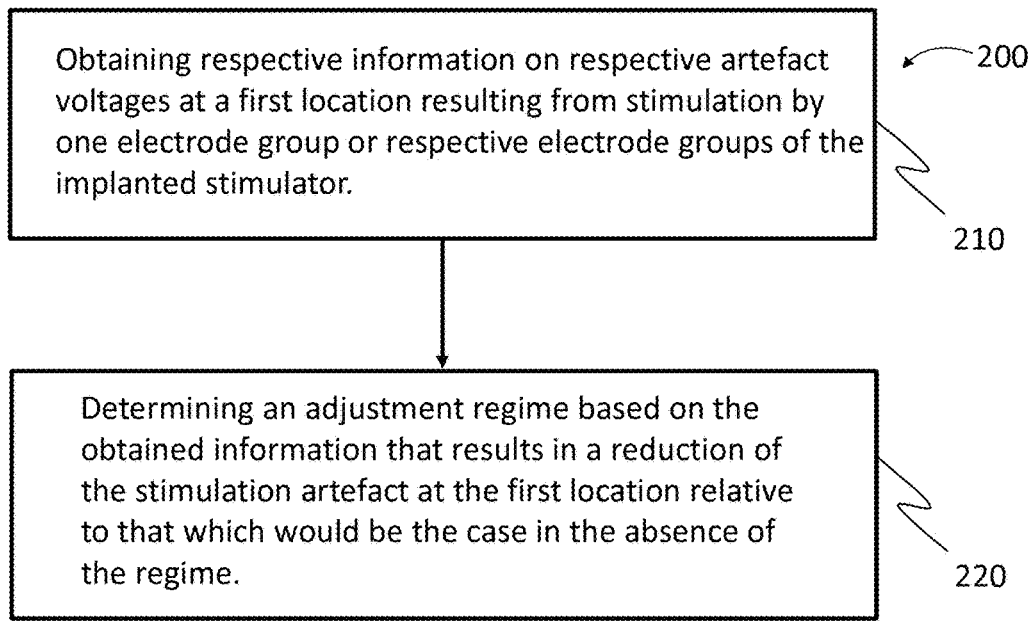
FIGS. 2A and 2B present exemplary flowcharts for exemplary algorithms according to exemplary embodiments.

FIG. 1 a is perspective view of a cochlear implant, referred to as cochlear implant 100, implanted in a recipient, to which some embodiments detailed herein and/or variations thereof are applicable. The cochlear implant 100 is part of a system 10 that can include external components, in some embodiments, as will be detailed below. It is noted that the teachings detailed herein are applicable, in at least some embodiments, to partially implantable and/or totally implantable cochlear implants (i.e., with regard to the latter, such as those having an implanted microphone). It is further noted that the teachings detailed herein are also applicable to other stimulating devices that utilize an electrical current beyond cochlear implants (e.g., auditory brain stimulators, pacemakers, etc.).

The recipient has an outer ear 101, a middle ear 105 and an inner ear 107. Components of outer ear 101, middle ear 105 and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear channel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown, cochlear implant 100 comprises one or more components which are temporarily or permanently implanted in the recipient. Cochlear implant 100 is shown in FIG. 1 with an external device 142, that is part of system 10 (along with cochlear implant 100), which, as described below, is configured to provide power to the cochlear implant, where the implanted cochlear implant includes a battery that is recharged by the power provided from the external device 142.

In the illustrative arrangement of FIG. 1, external device 142 can comprise a power source (not shown) disposed in a Behind-The-Ear (BTE) unit 126. External device 142 also includes components of a transcutaneous energy transfer link, referred to as an external energy transfer assembly. The transcutaneous energy transfer link is used to transfer power and/or data to cochlear implant 100. Various types of energy transfer, such as infrared (IR), electromagnetic, capacitive and inductive transfer, may be used to transfer the power and/or data from external device 142 to cochlear implant 100. In the illustrative embodiments of FIG. 1, the external energy transfer assembly comprises an external coil 130 that forms part of an inductive radio frequency (RF) communication link. External coil 130 is typically a wire antenna coil comprised of multiple turns of electrically insulated single-strand or multi-strand platinum or gold wire. External device 142 also includes a magnet (not shown) positioned within the turns of wire of external coil 130. It should be appreciated that the external device shown in FIG. 1 is merely illustrative, and other external devices may be used with embodiments of the present invention.

Cochlear implant 100 comprises an internal energy transfer assembly 132 which can be positioned in a recess of the temporal bone adjacent auricle 110 of the recipient. As detailed below, internal energy transfer assembly 132 is a component of the transcutaneous energy transfer link and receives power and/or data from external device 142. In the illustrative embodiment, the energy transfer link comprises an inductive RF link, and internal energy transfer assembly 132 comprises a primary internal coil 136. Internal coil 136 is typically a wire antenna coil comprised of multiple turns of electrically insulated single-strand or multi-strand platinum or gold wire.

Cochlear implant 100 further comprises a main implantable component 120 and an elongate electrode assembly 118. In some embodiments, internal energy transfer assembly 132 and main implantable component 120 are hermetically sealed within a biocompatible housing. In some embodiments, main implantable component 120 includes an implantable microphone assembly (not shown) and a sound processing unit (not shown) to convert the sound signals received by the implantable microphone in internal energy transfer assembly 132 to data signals. That said, in some alternative embodiments, the implantable microphone assembly can be located in a separate implantable component (e.g., that has its own housing assembly, etc.) that is in signal communication with the main implantable component 120 (e.g., via leads or the like between the separate implantable component and the main implantable component 120). In at least some embodiments, the teachings detailed herein and/or variations thereof can be utilized with any type of implantable microphone arrangement.

Main implantable component 120 further includes a stimulator unit (also not shown) which generates electrical stimulation signals based on the data signals. The electrical stimulation signals are delivered to the recipient via elongate electrode assembly 118.

Elongate electrode assembly 118 has a proximal end connected to main implantable component 120, and a distal end implanted in cochlea 140. Electrode assembly 118 extends from main implantable component 120 to cochlea 140 through mastoid bone 119. In some embodiments electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123 or through an apical turn 147 of cochlea 140.

Electrode assembly 118 comprises a longitudinally aligned and distally extending array 146 of electrodes 148, disposed along a length thereof. As noted, a stimulator unit generates stimulation signals which are applied by electrodes 148 to cochlea 140, thereby stimulating auditory nerve 114.

Because the cochlear implant 100 is implanted within the recipient, there is utilitarian value in obtaining information regarding the actual performance of the electrode array subsequent implantation into the cochlea and/or information regarding the response of the auditory nerve to stimulation. Such information collection can enable detection and confirmation of utilitarian operation of the cochlear implant, and/or allow stimulation parameters to be adjusted to suit the needs of the patient. For example, such can enable the cochlear implant to be fitted to the recipient.

More specifically, in an exemplary embodiment, subsequent implantation of the cochlear implant 100, the recipient can have the cochlear implant 100 fitted or customized to conform to the specific recipient desires. This procedure can collect information and determine patient specific parameters such as threshold levels (T levels) and maximum comfort levels (C levels) for one or more or all stimulation channels of the cochlear implant 100. In some embodiments, there is utilitarian value in obtaining objective measurements/information of recipient specific information, such as, by way of example only and not by way of limitation, in cases where an accurate subjective measurement is difficult, if not impossible (e.g., for an infant).

In some exemplary embodiments, there includes a method entailing interrogating the performance of the cochlear implant and making objective measurements of recipient specific data such as T and C levels, etc., by directly measuring the response of the auditory nerve to an electrical stimulus resulting from the cochlear implant 100. The measurement of Electrically Evoked Compound Action Potentials (ECAPs) can provide an objective measurement of the response of the nerves to electrical stimulus. In at least some exemplary embodiments, following electrical stimulation, the neural response is caused by the superposition of single neural responses at the outside of the axon membranes. The ECAP is then measured in response to various stimulations and from this the performance of the cochlear implant can be assessed and recipient parameters can be interpolated.

In an exemplary embodiment, there is utilitarian value in measuring the response of nerves to electrical stimulation in many applications. The measurement of ECAPs can provide a utilitarian objective measurement in many such applications. By measuring the ECAP in response to a stimulation, the effectiveness of the stimulation can, in at least some scenarios, be assessed in relation to the neural response evoked by the stimulation.

An exemplary embodiment utilizes ECAP measurement methods and apparatuses that measure or otherwise obtain information pertaining to the response of the nerves to electrical stimulus, and, in some embodiments, utilize various electrodes implanted within the cochlea to both deliver stimulation and to detect the responses of the nerves to such stimulation.

In some applications of ECAP measurement, there exists stimulus artefacts that can have a deleterious affect with respect to the quality of the measurements of the neural response. In at least some instances, this is a result of the presence of stimulus artefacts in the measurement, resulting in a measurement being taken which is not necessarily a true indication of the actual ECAP response present.

It is often difficult to distinguish the actual ECAP from stimulus artefacts. For example, the signals that are to be measured are extremely low level signals (for example and not by way of limitation, down to the order of 10 uV). In cochlear implant applications in particular, an intracochlear electrode usually delivers a stimulus pulse with an amplitude typically in the range of 1V to 10V, which is many orders of magnitude greater than the ECAP response that is to be measured resulting from this stimulation. Thus, the artefact resulting from the stimulus pulse "outshines" the actual ECAP in a manner analogous to placing a flashlight next to a search light.

In at least some instances, to resolve the relatively very small neural signal, a relatively large amplifier gain is required (e.g., about 60 dB to 70 dB). However, the neural signal is often superimposed on a much larger artefact which makes it difficult to extract the neural signal of interest due to the finite dynamic range of the amplifier and the typical demand for high gain to resolve the signal.

In an exemplary embodiment, the electrodes of the cochlear implant are utilized to null the artefact(s) at the recording location (the location where the ECAP is detected). In at least some exemplary embodiments, the recording location is at a recording electrode. In at least some embodiments, the recording electrode is implanted in the recipient, such as in the cochlea, while in other embodiments, the recording electrode is not implanted in the recipient (e.g., is located at the surface of the skin).

An exemplary embodiment includes utilizing the teachings detailed herein and/or variations thereof to increase the speed (e.g., double, or increase the speed even more than that corresponding to a doubling) of Neural Response Telemetry (NRT) by, for example, removal of the need for masker and masker and probe recordings. Alternatively and/or in addition to this, an exemplary embodiment includes utilizing the teachings detailed herein and/or variations thereof to increase the accuracy (e.g., double the accuracy, or increase the accuracy even more than that corresponding to a doubling) of Neural Response Telemetry (NRT) by, for example, removal of the need for masker and masker and probe recordings. Thus, an exemplary embodiment includes utilizing the teachings detailed herein and/or variations thereof without masker and/or masker in probe recordings. Alternatively and/or in addition to this, exemplary embodiments can include utilizing the teachings detailed herein and/or variations thereof to obtain NRT thresholds previously unobtainable within a given recipient's perceptual range (e.g., because providing a masker at 10 CL higher than the probe will not be required—thus, an exemplary embodiment includes utilizing the teachings detailed herein without a masker at 10 CL higher than the probe). Accordingly, embodiments include obtaining NRT thresholds while avoiding a need to near or exceed the loudest acceptable level, which can avoid or otherwise mitigate a need for anesthesia.

By not utilizing a masker, any need to attempt to optimize masker parameters (e.g., level, masker-probe interval, etc.) is negated. Accordingly, an exemplary embodiment includes implementing the teachings detailed herein without optimizing or otherwise adjusting masker parameters.

Still further, some embodiments include utilizing the teachings detailed herein such that a reduction in noise is achievable. This is because at least some exemplary embodiments utilize the teachings detailed herein without summing four independent sources of noise, and thus the computational time is reduced. Indeed, in at least some exemplary embodiments include utilizing the teachings detailed herein to obtain higher gain settings, thereby potentially improving the signal to noise ratio, all relative to that which would be the case in the absence of utilizing the teachings detailed herein and/or variations thereof in a NRT method.

Some exemplary methods relating to nulling of the artefacts will now be described.

In an exemplary method, there is a method entailing utilizing multipolar stimulation by an implanted stimulator, such as a cochlear implant or other type of implanted stimulator, to reduce (including eliminate) stimulation artefacts in the neural response telemetry (NRT). For example, FIG. 2A details an exemplary flowchart for an exemplary method 200 which entails actions 210 and 220. Action 210 entails obtaining respective information on respective artefact voltages at a first location resulting from stimulation by one electrode group or respective electrode groups of of an implantable (including an implanted) stimulator. More particularly, in an exemplary embodiment, action 210 entails obtaining respective properties of respective electrical voltages resulting from respective stimulating electrical currents emanating from respective one or more electrodes of respective electrode group(s).

Before going further, it is noted that while the focus of the teachings detailed herein is directed towards an implanted cochlear implant, it is further noted that the teachings detailed herein and/or variations thereof are also applicable, in some embodiments, to situations where the methods are executed during a pre-operation procedure and/or during surgery (intra-operation), where, for example, the electrodes are inserted in the recipient (or implanted in the recipient) but other components of the implant are not yet inserted or implanted in the recipient (e.g., the electrode array is inserted into the cochlea, but the leads to the receiver/stimulator extend outside the recipient because the receiver/stimulator has not yet been inserted and/or implanted in the recipient, which may be utilitarian because the surgeon desires to first test the implant prior to fully implanting the implant). Indeed, in some instances, even after electrode implantation, the leads may extend outside the recipient to a device that provides electrical current to the electrodes.

It is further noted that while the focus of the teachings detailed herein is directed towards a cochlear implant, these teachings are applicable to any device or system or method that utilizes electricity to stimulate tissue (e.g., an auditory brain stimulator, a pacemaker, etc.), providing that such application provides utilitarian value.

Figure 2B:
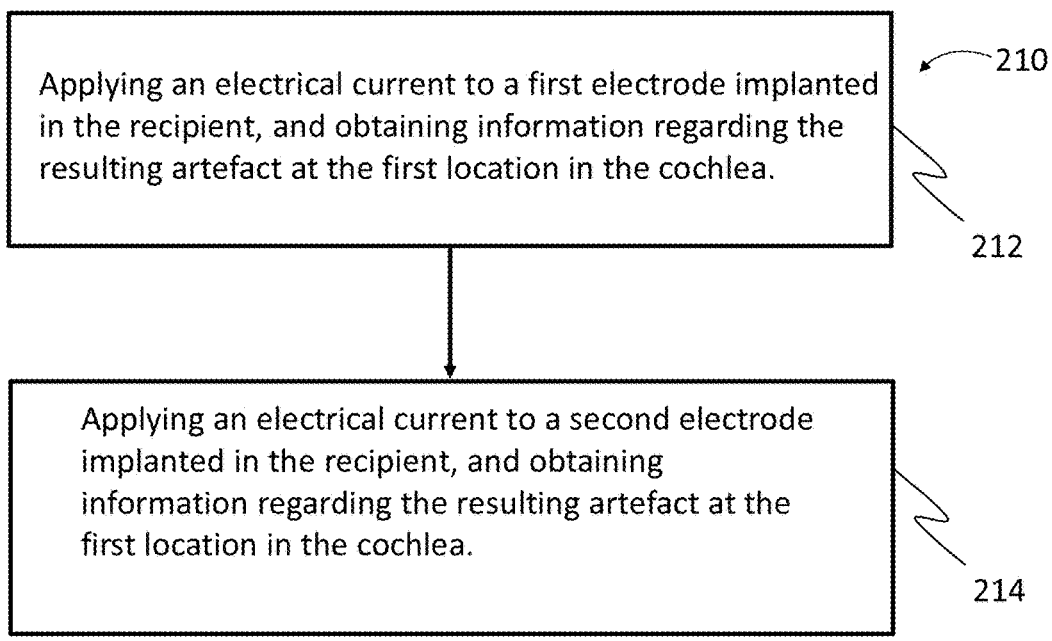
Figure 3A:
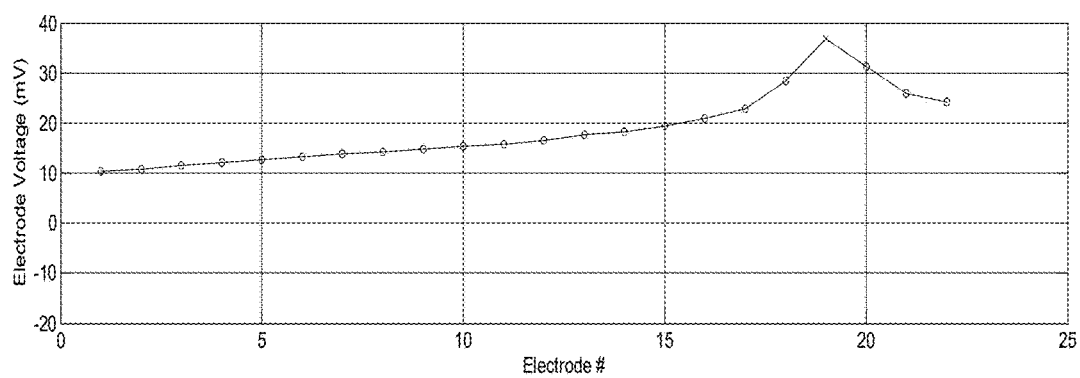
FIGS. 3A-3D present exemplary graphics in support of descriptions of some exemplary embodiments.
Figure 3B:
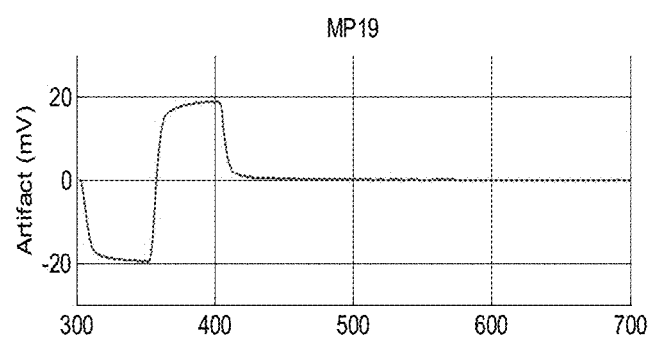

In an exemplary embodiment, method action 210 entails sub-actions 212 and 214 as detailed in FIG. 2B. Sub-action 212 entails applying an electrical current to a first electrode implanted in the recipient, and obtaining information regarding the resulting artefact at the first location in the cochlea. In an exemplary scenario, the electrical current is applied at electrode 19 of a 22 electrode cochlear electrode array at 50 CL (current level using the CIC3 scale) and the first location corresponds to the location of a recording electrode, which, for example, can be electrode 16 of the aforementioned 22 electrode cochlear electrode array. The results of the application of the current to electrode 19 with a return electrode located at an extracochlear location is present in FIG. 3A (electrode 19 and the return electrode corresponding to a first electrode group), which depicts an exemplary artefact at the locations of the other 21 electrodes of the electrode array. (Recording at electrode 16 would record an artefact of 20,839 uV for the 50 CL applied to electrode 19, at least in the absence of the innovative nulling detailed herein.) FIG. 3B depicts time-based values of the artefact at the recording electrode, on a millivolt scale, for a time period extending from 300 microseconds to 700 microseconds.

Figure 4:
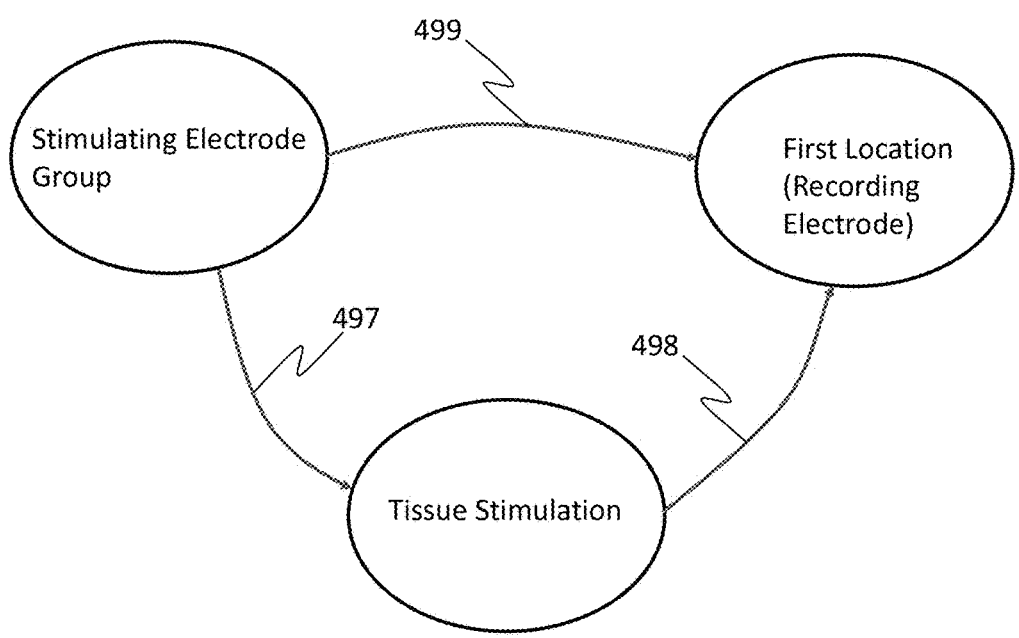
FIGS. 4 and 5 functionally depict respective exemplary methods.

Functionally, sub-action 212 is depicted in FIG. 4, where arrow 497 indicates the desired tissue stimulation from the respective stimulating electrode group, arrow 498 indicates the voltage from the desired tissue stimulation that is recorded at the first location, and arrow 499 indicates unwanted artefact voltage from the stimulating electrode.

Sub-action 214 entails applying an electrical current to a second electrode implanted in the recipient, separate from the first electrode of sub-action 212, and obtaining information regarding the resulting artefact at the first location in the cochlea. In an exemplary scenario, the electrical current is applied at electrode 15 of the 22 electrode cochlear electrode array at 50 CL (current level) with an inverted phase relative to that of sub-action 212, and the first location corresponds to the location of a recording electrode, which, continuing with the example presented above, is electrode 16 of the aforementioned 22 electrode cochlear electrode array. The results of the application of the current to electrode 15 with a return electrode located at an extracochlear location is present in FIG. 3C (which in this embodiment is the same return electrode as that detailed in the above scenario vis-à-vis sub-action 212—electrode 15 and the return electrode corresponding to a second electrode group), which depicts an exemplary artefact at the locations of the other 21 electrodes of the electrode array. (Recording at electrode 16 would record an artefact of −28,026 uV for the 50 CL applied to electrode 15.) FIG. 3D depicts time-based values of the artefact at the recording electrode, on a millivolt scale, for a time period extending from 300 microseconds to 700 microseconds In at least some embodiments, FIG. 4 corresponds to sub-action 214 as well (i.e., the respective stimulating electrode group corresponds to first electrode group for sub-action 212, and second electrode group for sub-action 214).

It is noted that in at least some embodiments, action 210 can include one or more additional sub-actions beyond sub-actions 212 and 214. In an exemplary embodiment, action 210 can include three, four, five, six, seven or more sub-actions. In at least some exemplary embodiments, the sub-actions respectively entail applying electrical current to an electrode implanted in the recipient. By way of example only and not by way of limitation, continuing with the exemplary sub-actions of FIG. 2B, an exemplary embodiment include additional sub-action(s) where respective current(s) are applied to respective different electrodes different from electrode 15 and electrode 19 and respective electrode(s) to which current was applied of different sub-actions (e.g., sub-actions that include the application of current to one or more of the other electrodes on the cochlear electrode array, at least other than the recording electrode 16).

As noted above, sub-action 214 entails applying an electrical current to a second electrode that is separate from the first electrode to which electrical current is applied in sub-action 212. As detailed above, the respective electrode groups of sub-actions 212 and 214 include at least one electrode that is the same (the return electrode). Thus, while the respective electrode groups are different, they share a common electrode.

That said, in an alternate embodiment, the electrode group used to execute sub-actions 212 and 214 (or any additional sub-actions that may be included in action 21) comprises the same electrodes. In this regard, in an exemplary embodiment, the information obtained by execution of method action 210 entails information resulting from stimulation by the same electrode group. That is, method sub-actions 212 and 214 (and/or additional sub-actions, in embodiments that include such additional sub-actions) entail applying respective electrical currents to electrodes of the same group. By way of example only and not by way of limitation, in an exemplary scenario relating to implementation of sub-actions 212 and 214, the electrical current is applied at electrode 19 of a 22 electrode cochlear electrode array at 50 CL, with the return current being electrode 14 of the 22 electrode cochlear electrode array. The first location corresponds to the location of a recording electrode, which, for example, can be electrode 17 of the aforementioned 22 electrode cochlear electrode array. In this exemplary scenario, sub-action 214 entails applying an electrical current to electrode 14 of the 22 electrode cochlear electrode array at 50 CL (current level) with an inverted phase relative to that of the just-described exemplary scenario of sub-action 212, with the return current being electrode 19 of the 22 electrode cochlear electrode array. Thus, in at least some embodiments, the respective artefacts obtained in method action 210 at the first location result from stimulation by one electrode group/the same electrode group, and the one electrode group comprises only intracochlear electrodes. In the just described scenario, it can be seen that the one electrode group comprises only two electrodes. However, in an alternate embodiment, the one electrode group can comprise three or more electrodes.

Figure 6A:
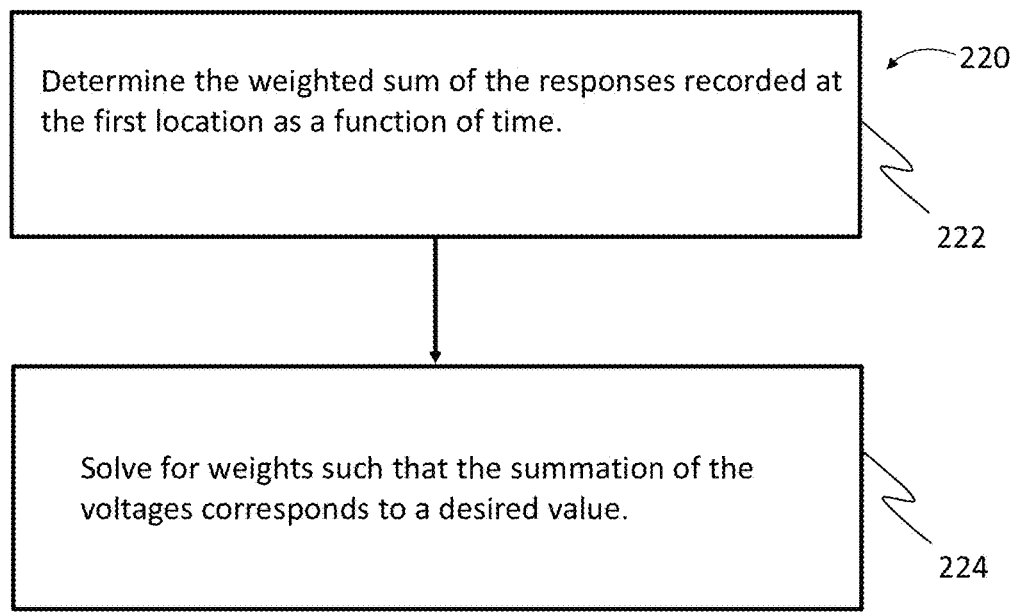
FIGS. 6A and 6B present exemplary flowcharts for exemplary algorithms according to exemplary embodiments.
Figure 6B:
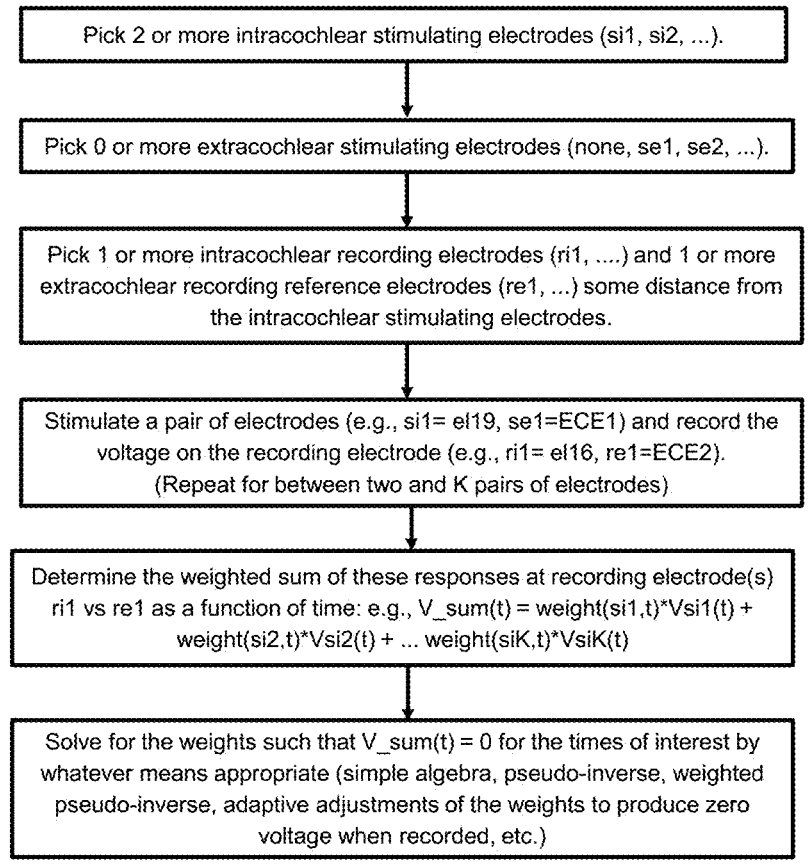

FIG. 6B depicts an exemplary algorithm for an exemplary embodiment of method 200 based on a weighting regime used with a cochlear implant.

In at least some embodiments, any number of electrodes in any combination located at any location that can enable the teachings detailed herein and/or variations thereof to be practiced with utilitarian value can be utilized in at least some embodiments.

Indeed, in at least some embodiments, one or more of the electrodes utilized to execute a portion of method action 210 can be electrodes of a separate apparatus from those utilized to execute a portion of method action 210. By way of example only and not by way of limitation, with respect to the first location, the first location can be a location corresponding to a separate apparatus from that which provides current to the stimulating electrodes. For example, the recording electrode can be an electrode that is part of an apparatus that is different from the implanted stimulator used to stimulate the stimulating electrodes. By way of example only and not by way of limitation, the recording electrode of a recording apparatus, separate from the implanted stimulator (e.g. an auditory brain stimulator), can be an electrode placed on the scalp of a recipient of the implanted stimulator. Alternatively, and/or in addition to this, the recording electrode can be inserted into the recipient as well (e.g., temporarily or permanently).

It is noted that in some exemplary embodiments, sub-action 212 is executed during a different temporal period from that of method sub-action 214. Accordingly, in an exemplary embodiment, the respective information obtained from the respective sub-actions is obtained at respective different temporal periods. In an exemplary embodiment, the temporal periods do not overlap, while in other embodiments, the temporal periods overlap. In some exemplary embodiments, the temporal periods follow one another without an intervening temporal period, while in other embodiments, there are temporal periods interposed between the respective temporal periods. It is noted that in some alternate embodiments, the sub-actions 212 are executed during the same temporal periods.

In an exemplary embodiment, the information obtained from the sub-actions is a voltage measurement. That is, the recording electrode(s) obtain information about the voltage of the current at the recording electrode(s). It is noted that in some embodiments, the voltage(s) is measured directly, while in alternate embodiments, the voltage is measured indirectly. Any device, system and/or method that can enable the voltage at the locations of interest (e.g., the first location/the voltage at the recording electrode(s)) to be ascertained can be utilized in at least some embodiments.

As noted above, again with reference to FIG. 2A, method 210 includes sub-action 220. This entails determining an adjustment regime based on the obtained information from method 210. In sub-action 220, the determined adjustment regime is one that results in a reduction of the stimulation artefact at the first location relative to that which would be the case in the absence of the adjustment regime. Some exemplary embodiments of the adjustment regime will now be described, but first, an exemplary nulling method will be briefly described, by which exemplary nulling method the determined adjustment regime can be implemented.

Figure 5:
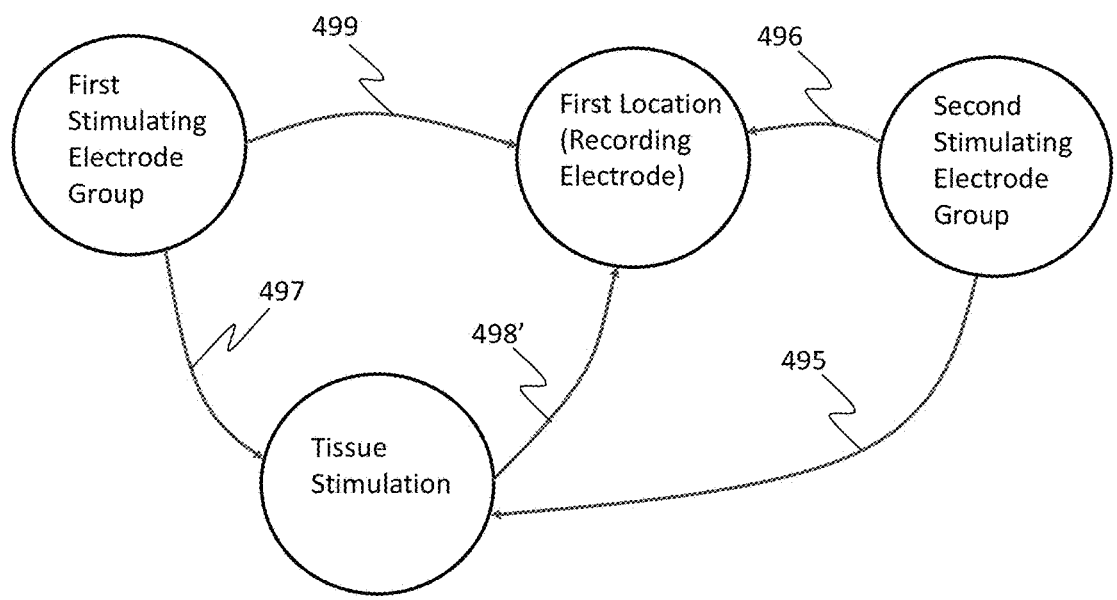

FIG. 5 depicts a functional schematic of implementation of an exemplary nulling method according to an exemplary embodiment, where the first and second stimulating electrode groups correspond to the above-noted first and second electrode groups. Arrows 497 and 499 correspond to those of FIG. 4. Arrow 496 corresponds to a desired (as opposed to an unwanted) artefact voltage from the stimulating electrode of the second stimulating electrode group. Arrow 495 corresponds to tissue stimulation from the second stimulating electrode group (which may not be present in some embodiments). Arrow 498' corresponds to the combined voltage from the tissue stimulation that is recorded at the first location due to the first stimulating electrode group and the second stimulating electrode group.

In the nulling method functionally depicted in FIG. 5, the addition of the second stimulating electrode group introduces a second artefact at the first location. In at least some embodiments, the aforementioned adjustment regime (which is described in greater detail below) is used to adjust the output of the stimulating electrodes and/or adjust the location of the recording electrode or stimulating electrode such that the artefacts resulting from the first stimulating electrode group and the second stimulating electrode group null one another (or, more accurately, the artefact from the second stimulating electrode group nulls that of the first stimulating electrode group, at least partially).

It is noted that the aforementioned adjustment can have an effect on the stimulated tissue which, in some instances, which will alter the ECAP by some amount. In an exemplary embodiment, the adjustment regime is such that the alteration to the ECAP, relative to the absence of the adjustment regime and/or the application of the stimulation from the second group of electrodes, is such that, the ECAP is minimally altered or effectively not altered (which includes not altered and includes alteration that does not affect the interpretation of the ECAP). Alternatively or in addition to this, the ECAP is altered in such a way so as to produce a response that results from a more focused stimulation, thus resulting in a reduced artifact ECAP with additional benefits for analyses such as neural diagnostics relative to that which would be the case in the absence of the alteration.

Now with reference back to the adjustment regime that is developed via sub-action 214, in an exemplary embodiment, the adjustment regime is weighting regime in general, and a current weighting regime in particular. Some exemplary embodiments of developing the adjustment regimes as exemplified by a current weighting regime will now be detailed.

FIG. 6A details various exemplary sub-actions of method action 220. The exemplary sub-actions of FIG. 6A are directed towards determining an adjustment regime based on the obtained information from method action 210 where two different groups of electrodes are utilized to obtain the information. In particular, the scenario described above where intra-cochlear electrode 19 and an extra cochlear electrode corresponds to a first group of electrodes, and intra-cochlear electrode 15 and the extra cochlear electrode corresponds to a second group of electrodes. Further, the exemplary sub-actions of method action 200 depicted in FIG. 6A are based on a scenario where the determined information corresponds to voltage responses as a function of time recorded at the first location (the recording electrode).

More particularly, method action 220 includes sub-action 222, which entails determining the weighted sum of the voltage responses recorded at the first location as a function of time. In an exemplary embodiment, an algorithm for executing sub-action 222 can be $$V\_sum(t) = \text{weight}(si1,t) * Vsi1(ri1,t) + \text{weight}(si2,t) * Vsi2(ri1,t)$$

where si1 corresponds to the number of the intra-cochlear electrode to which current is applied in sub-action 212 (e.g., electrode 19), Vsi1(ri1,t) corresponds to the artefact voltage produced at electrode ri1 by stimulation of si1, si2 corresponds to the number of the intra-cochlear electrode to which current is applied in sub-action 214 (e.g., electrode 15), Vsi2(ri1,t) corresponds to the artefact voltage produced at electrode ri1 by stimulation of si2. With respect to the exemplary scenarios detailed above, Vsi1(ri1,t) can be graphically depicted as depicted in FIG. 3B, and Vsi2(ri1,t) can be graphically depicted as depicted in FIG. 3D.

In exemplary embodiments which include additional sub-actions of method action 210, an algorithm for executing sub-action 222 can be $$V\_sum(t) = \text{weight}(si1,t) * Vsi1(ri1,t) + \text{weight}(si2,t) * Vsi2(ri1,t) + \text{weight}(siK,t) * VsiK(ri1,t)$$

where siK corresponds to the number of the intra-cochlear electrode to which current is applied in sub-action K and VsiK(ri1,t) corresponds to the voltage of that electrode, where additional terms representing other K values could be added for each current source.

After determining the weighted sum of the responses in sub-action 222, sub-action 224 is executed, which entails solving for weights such that V_sum(t) corresponds to a desired value. In an exemplary embodiment, V_sum(t)= zero. In alternative embodiments, the desired value is such that V_sum(t) is effectively zero, or closer to zero than that which would be the case without the weighting. Any values for V_sum(t) which will enable the teachings detailed herein and/or variations thereof to be practiced can be utilized in at least some embodiments.

It is noted that the solution for the weights in method sub-action 224 can be achieved utilizing any device, system, and/or method that can enable the teachings detailed herein and/or variations thereof to be practiced. By way of example only and not by way of limitation, one exemplary method for solving for the weights in method sub-action 224 entails utilizing algebra (simple and/or complex), pseudo-inverse (weighted and/or non weighted) adaptive adjustments of the weights to produce the desired voltage, etc.

It is further noted that in at least some embodiments, the aforementioned desired value(s) for V_sum(t) is the value that is recorded at the first location (e.g., the recording electrode(s)).

In view of the above, it can be seen that at least some embodiments entail adjustment regimes where adjustments are made to the current applied to electrodes and/or electrode selection (including selecting a particular recording electrode) to adjust the voltage at the recording electrode of the cochlear implant towards zero. In some exemplary embodiments, the artefact voltage at the recording electrode is substantially zero (which includes zero). That said in some exemplary embodiments, the voltage at the recording electrode is a value that is substantially lower than that which would be the case in the absence of the adjustment regime.

In an exemplary embodiment, method sub-action 224 entails solving for weights such that the desired voltage summation is for specific times of interest. That is, the summation may be for a subset of the recorded times. By way of example only and not by way of limitation, the times of interest may be between 400 μs and 600 μs. Additional details of embodiments associated with times of interest are detailed below.

Continuing with respect to the exemplary scenarios detailed above, if Vsi1(ri1,t) corresponds to that of FIG. 3B, and Vsi2(ri1,t) corresponds to that of FIG. 3D, method sub-action 224 results in a weighting of the current from electrode si2 (i.e., electrode 15 with respect to the current scenario) corresponding to 0.7 and a weighting of the current from electrode si1 (i.e., electrode 19 with respect to the current scenario) corresponding to 1.0. It is noted that in alternate scenarios, the weighting of si1 might be different from 1.0, and the weighting of si2 might be 1.0. Any weighting that is arrived at that can enable the teachings detailed herein and/or variations thereof to practice can be utilized in at least some embodiments.

Figure 7A:
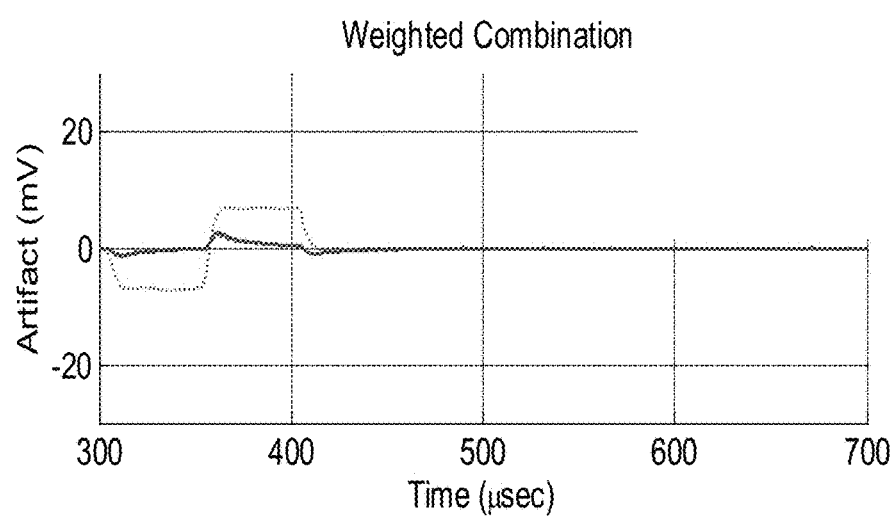
FIGS. 7A-7D present exemplary graphics in support of descriptions of some exemplary embodiments.

FIG. 7A depicts time-based values of the artefact at the recording electrode, on a millivolt scale, for a time period extending from 300 microseconds to 700 microseconds, when stimulation from electrode si2 is weighted by 0.7 (weight(si2,t)=0.7), and stimulation from electrode si1 is weighted by 1.0 (weight(si1,t)=1.0) (i.e., the current output by si2 is 15 CL less than that of si1, which is 50 CL), and the stimulations are applied during effectively identical temporal periods. In this regard, FIG. 7A depicts an example corresponding to the results of implementation of the method functionally represented by FIG. 5 (this is discussed in greater detail below with respect to current levels applied to electrodes to evoke a neural response (which can be elevated with respect to the current levels used to develop the adjustment regime)).

It is noted that the weighting values detailed herein (e.g., k=0.7, k=0.5, etc., as detailed below) are exemplary values provided for purposes of illustrating the underlying concepts herein. It is further noted that for linguistic efficiency, the weightings described in the next few paragraphs will be described in terms of the weighting of the second electrode, and unless otherwise specified, the weighting of the first electrode will be 1.0. Any weighting values that can enable the teachings detailed herein and/or variations thereof to be practiced can be utilized in at least some embodiments.

As can be seen from FIG. 7A, in comparison to FIG. 3B, the artefact at the recording electrode is substantially reduced relative to that which was the case with respect to stimulation by only electrode si1.

Thus, continuing with respect to this exemplary scenario, the resulting determined adjustment regime based on the obtained information from method action 210 is a regime in which current from the second electrode si2 is weighted by 0.7 (weight(si2,t)=0.7), and applied simultaneously to that electrode as current weighted by 1.0 (weight(si1,t)=1.0) is applied to first electrode si1, as these weightings are weightings that result in a reduction of the stimulation artefact at the first location relative to that which would be the case in the absence of the weighting regime. In this regard, the weighting of the regime is such that when at least one of the first and second electrical currents is adjusted by the regime (adjusted from a base current level which would be applied to both equally), the result is at least effective cancellation of voltage at the at least one recording electrode, as is depicted in FIG. 7A.

As noted above, the adjustment regimes can be varied based on times of interest. Adjustment regimes can also be based on the magnitude (peak) of the response. In at least some embodiments, the times of interest can be different depending on a given situation. Some exemplary scenarios will now be detailed with respect to graphs of recorded voltages at the recording electrodes on the microvolt scale. In this regard, FIG. 7B corresponds to FIG. 3B, and depicts time-based values of the artefact at recording electrode 16, on a microvolt scale, for a time period extending from 300 microseconds to 700 microseconds. FIG. 7C corresponds to FIG. 3D, and depicts time-based values of the artefact at recording electrode 16, on a microvolt scale, for a time period extending from 300 microseconds to 700. FIG. 7D corresponds to FIG. 7A, and depicts time-based values of the artefact at recording electrode 16, on a microvolt scale, for a time period extending from 300 microseconds to 700 microseconds. It is noted that the graph for k=0.7 (i.e., weight(si2,t)=0.7, weight(si1,t)=1.0—again, as noted above, these paragraphs focus on the weighting of the second electrode for linguistic economic reasons) includes two curves, one for the recorded values and one for the predicted values (because the recorded and predicted values track each other relatively similarly, the differences between the two will not be described—it is noted that FIG. 7A also includes two curves for k=0.7, but the differences are essentially graphically imperceptible on the millivolt scale (as opposed to the microvolt scale of FIG. 7D).

Figure 7B:
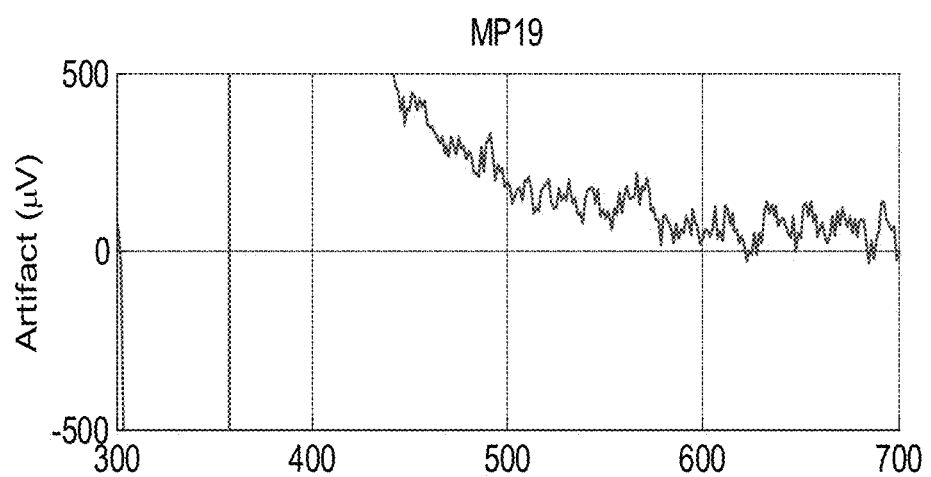
Figure 7C:
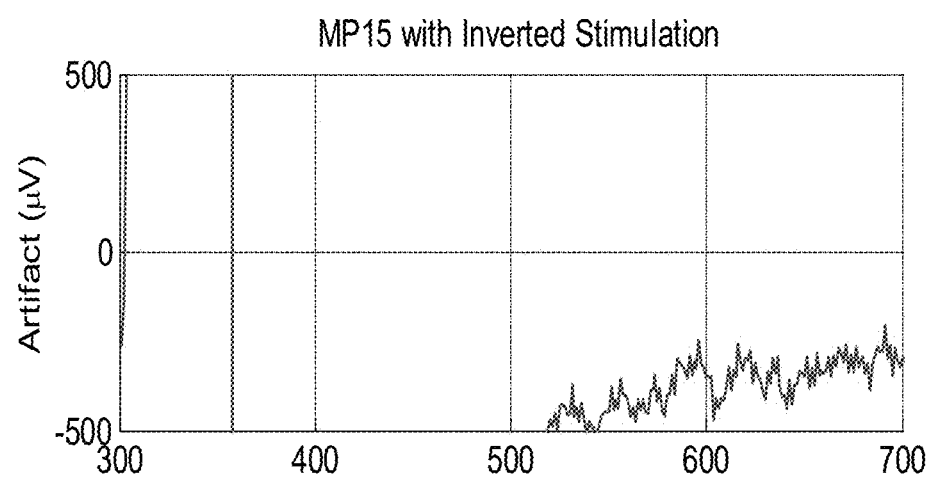
Figure 7D:
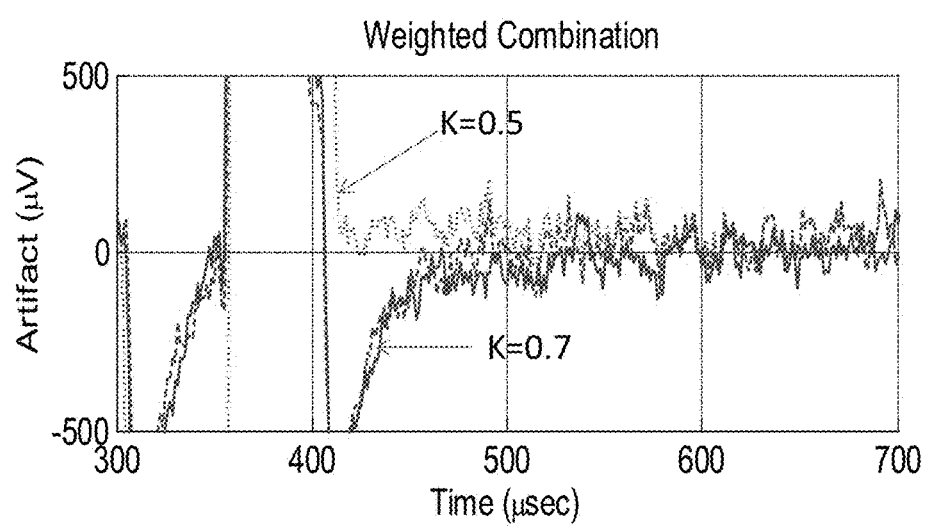

From FIGS. 7B and 7C, it can be seen that the artefacts recovered to zero more slowly than that which is the case in FIG. 7D, where the noise floor is reached much more rapidly, well before 600 μs, as can be seen. Further, as can be seen in FIG. 7D, the artefact at the recording electrode for the weighted combination where k equals 0.5 (weight(si2,t)=0.5, weight(si1,t)=1.0) returns to zero (or, more accurately, stabilizes at values closer to zero) about 50 μs prior to that which is the case where k equals 0.7 (weight(si2,t)=0.7, weight(si1,t)=1.0). Accordingly, if some embodiments may have utility in utilizing the weighting where k equals 0.5 for the second electrode as opposed to the weighting where k equals 0.7 for the second electrode (both cases k equals 1.0 for the first electrode), even though the weighting where k equals 0.7 results in an artefact that is substantially lower in totality over the period of time from, for example 300 μs to 500 μs, as can be seen from FIG. 7A. Alternatively, if the timeframe of interest is between 300 microseconds and 400 microseconds, the weighting of k=0.7 can have more utilitarian value, in at least some embodiments.

Still further, in view of the exemplary scenarios just noted, in the event that it is desired to reduce the peak of the response at the recording electrode an adjustment regime utilizing k=0.7 for the second electrode as opposed to k=0.5 for the second electrode (both cases k equals 1.0 for the first electrode) would be utilized. Conversely, in the event that it is desired to obtain a relatively faster recovery to zero, an adjustment regime utilizing k=0.5 as opposed to k=0.7 would be utilized.

Again, it is noted that the examples of weighting values (k values) are just that, examples. Any weighting value can be used to enable the teachings detailed herein and/or variations thereof.

Still further, in view of the above, at least some embodiments include an adjustment regime where the weighting is variable depending on the given temporal period. In this regard, the weights can be time-varying weights. By way of example only and not by way of limitation, with respect to the examples detailed in FIG. 7D, an exemplary adjustment regime can entail utilizing a value of k equaling 0.7 at the second electrode during a first time period, and a value of k equaling 0.5 at the second electrode during a second time period (e.g., immediately after the first time period), where in both cases, the weighting of the first electrode is 1.0.

Figure 8:
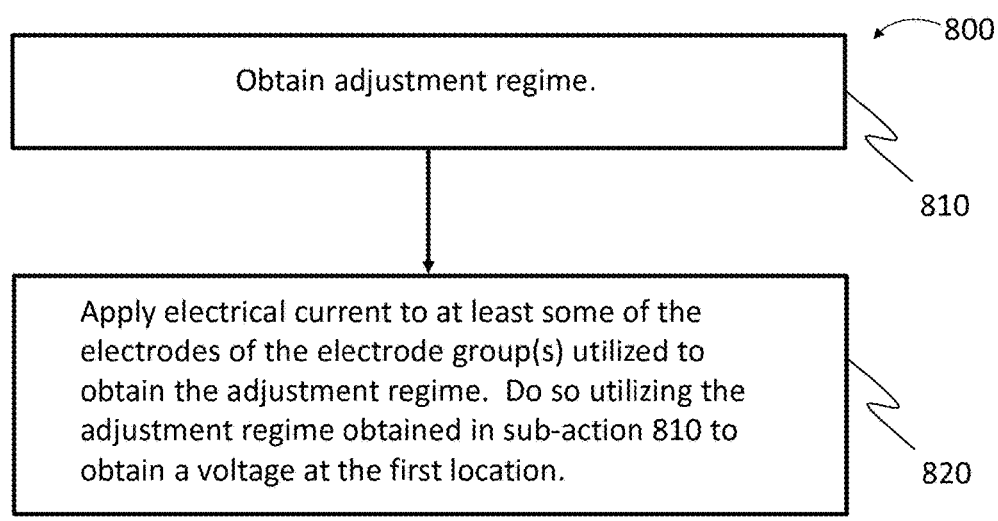

FIG. 8 depicts an exemplary method 800 which entails method sub-actions 810 and 820. Method sub-action 810 entails obtaining the adjustment regime, which can be accomplished by any of the methods detailed herein and/or variations thereof. Method sub-action 820 entails applying electric currents simultaneously to at least some and/or to all of the electrodes of the electrode group(s) utilized to obtain the adjustment regime. This action further entails doing so utilizing the obtained adjustment regime obtained in sub-action 810 to obtain a voltage (i.e., the artefact) at the first location (i.e., the recorded voltage at the recording electrode). In an exemplary embodiment, this obtained voltage is a test voltage/a voltage that is usable to evaluate the adequacy of the adjustment regime, as will now be described.

Figure 9:
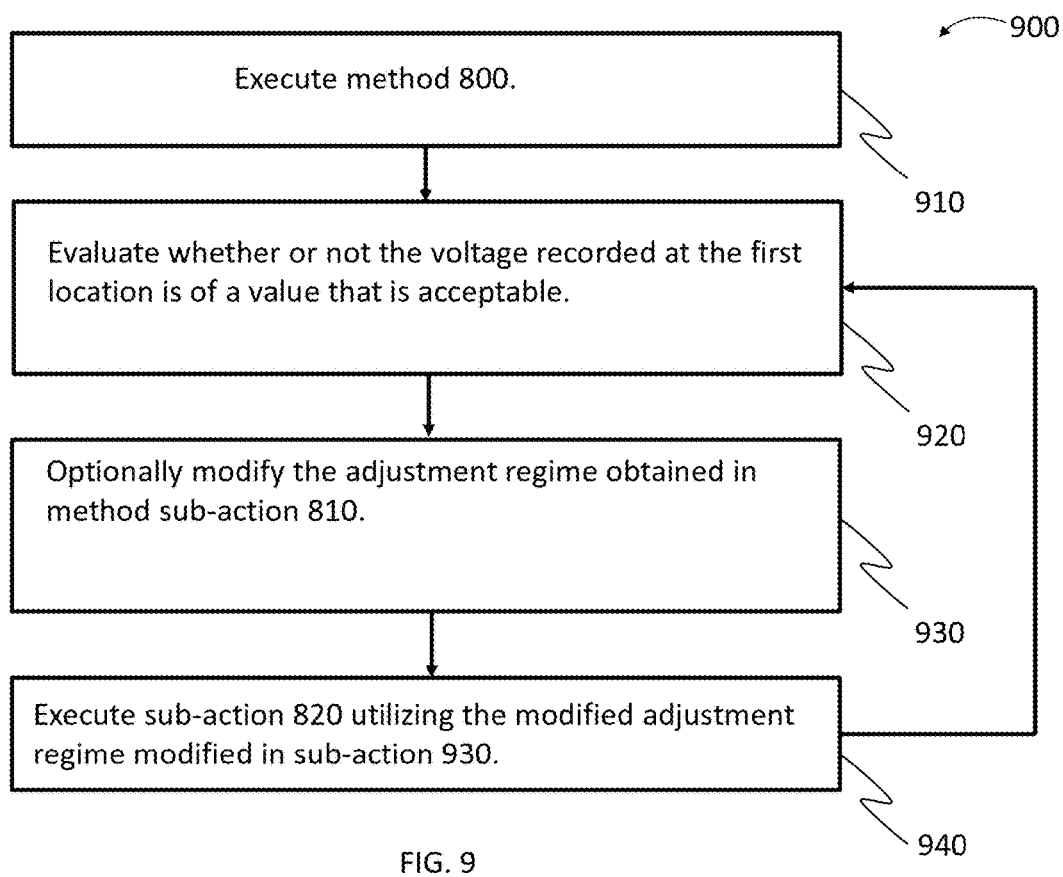

FIG. 9 presents an exemplary method 900 which entails sub-actions 910 and 920. Sub-action 910 corresponds to executing method 800. Sub-action 920 entails evaluating whether or not the voltage (i.e., the artefact) recorded at the first location (e.g., at the recording electrode) is of a value that is acceptable (e.g., low enough/below a maximum threshold). Method 900 includes optional sub-actions 930 and 940. In an exemplary embodiment, method sub-action 920 entails obtaining information on voltage at the first location resulting from the stimulation at the current levels utilized to execute sub-action 820.

Sub-action 930 is executed upon a determination at sub-action 920 that the voltage recorded at the first location is of a value that is unacceptable (e.g., above a maximum threshold). Method sub-action 930 entails modifying the adjustment regime obtained in method sub-action 810 when executing method 800 of sub-action 910. For example, if the obtained information is indicative of a voltage that exceeds a threshold (whatever that threshold may be), nullity weighting information of the regime is adjusted and/or new nullity weighting information is developed based on the obtained information such that the voltage at the first location is decreased from that of the obtained information. Method sub-action 940 corresponds to executing method sub-action 820 utilizing this modified adjustment regime. For example, method sub-action 940 can be executed using the respective new nullity weighting information as the nullity weighting information of the just-described example. After executing method sub-action 940, method 900 returns to method sub-action 920, which is again executed. This loop can be repeated until a determination is made at method sub-action 920 that the voltage recorded at the first location is a value that is acceptable, at which point method 900 can be terminated.

It is noted that in at least some exemplary embodiments, method 900, which includes the various other methods incorporated therein as detailed above (e.g., some or all of the actions of method 800, etc.), is executed such that (i) a neural response is not present, or at least not detectable and/or (ii) the recipient has no conscious perception that the electrodes are being stimulated (e.g., a hearing percept) and/or (iii) the recipient has a conscious perception that the electrodes are being stimulated. That said, some embodiments include method 1000 of FIG. 10A, as will be detailed below. However, it is noted that some embodiments include executing method 900 and/or some sub-actions thereof in an automatic manner as part of a routine that is included in a cochlear implant (although it is noted that the automatic manner can be initiated by input from the recipient and/or an audiologist etc.) By way of example only and not by way of limitation, some or all portions of method 900 can be executed while the recipient is sleeping or otherwise in a state where the recipient is not utilizing his or her cochlear implant to evoke a hearing percept (e.g. an inactive state). This can have utility in that, as detailed herein, some or all of the actions of method 900 can be executed below a threshold state (i.e., the recipient will not hear or otherwise notice that the method actions are being executed). In this regard in an exemplary embodiment entails executing some or all portions of method 900 and recording or otherwise storing the results of the actions in a database in the cochlear implant and/or in a remote location. In this regard, an extensive database can be developed of utilitarian adjustment regimes that can be later used by an audiologist or the like to execute some of the other methods detailed herein and/or variations thereof (such as by way of example only and not by way of limitation, methods 1000, 1100 and/or 1200, etc., which are detailed below). In the aforementioned extensive database can be developed well prior to the recipient visiting the audiologist, and thus saving time during the audiologist visit and/or permitting the audiologist to utilize the time available to perform other method actions. That said, it is noted that all are some portions of method 900 can be executed at the audiologist/during the audiologist visit.

Accordingly, in an exemplary embodiment, there is a method that entails executing some or all portions of method 900 during inactive states of the cochlear implant and/or during active states of the cochlear implant while the cochlear implant is not evoking a hearing percept and/or during active states of the cochlear implant while the cochlear implant is evoking a hearing percept. Exemplary method further includes developing a database of the adjustment regimes resulting from the execution of some or all portions of method 900 as just detailed. Exemplary method further includes downloading the data of the database to an audiologist, whereby the audiologist executes one or more or all of methods 1000, 1100, and/or 1200 (which are detailed below).

More particularly, method 1000 entails method sub-action 1010, which entails obtaining the adjustment regime either by executing method 900 and/or executing method 200 and/or obtaining the adjustment regime via another method (e.g., from data (e.g., records) developed by executing method action 900 and/or 200, etc.). In an exemplary embodiment, with respect to application of method 1000 with respect to a cochlear implant, this entails obtaining nullity weighting information based on artefact voltages at the first location in the cochlea for at least one current level of a plurality of respective first current levels respectively applied to respective electrodes of the cochlear implant.

Method 1000 also entails method sub-action 1020, which entails raising the current level of pertinent electrodes all by the same factor and applying electric currents simultaneously to at least some and/or to all of the electrodes (which correspond to the just mentioned "pertinent electrodes") of the electrode group(s) utilized to obtain the adjustment regime utilizing the adjustment regime (but at the raised current level) and applying the current to the electrodes, thereby resulting in electrical stimulation of the tissue of the recipient.

Figure 10A:
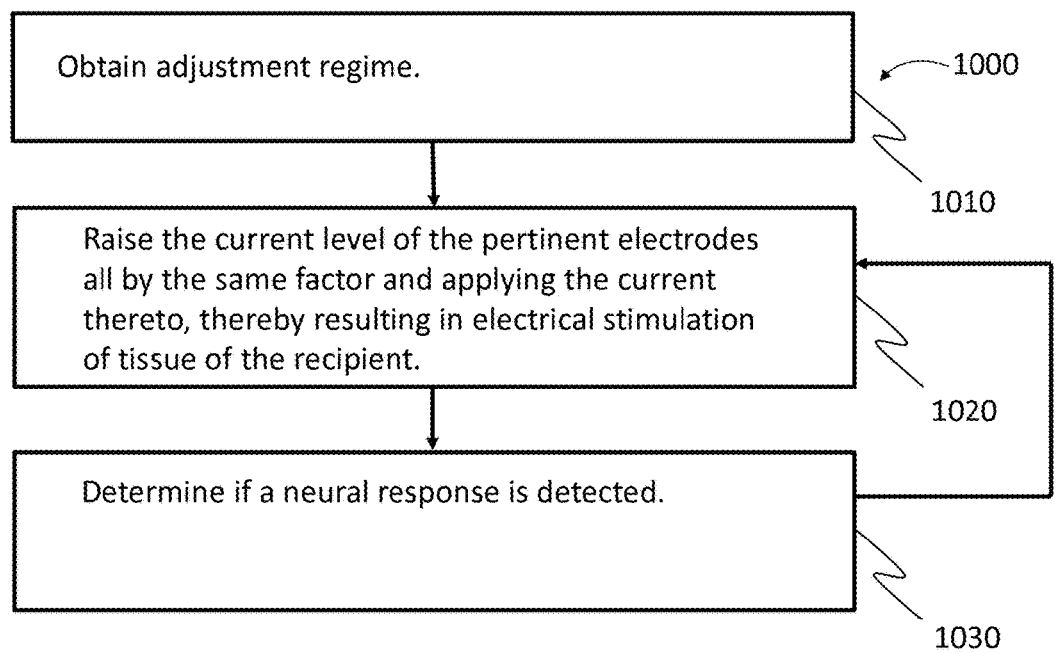

As can be seen from FIG. 10A, method 1000 includes method sub-action 1030, which entails determining if a neural response is detected (resulting from the application of the current in sub-action 1020). If the determination at sub-action 1030 is negative (i.e., a neural response is not detected) or otherwise indeterminable, method sub-actions 1020 and 1030 are repeated until a determination is made that a neural response has been detected (resulting from the application of the current in sub-action 1020. That said, in an alternate embodiment, action 1020 can be achieved by raising the current level of the pertinent electrodes by a factor that is different from one another, depending on the circumstances.

In an exemplary embodiment, method sub-action 1020 is executed by simultaneously stimulating the respective electrodes of method sub-action 1010 at respective second current levels such that a neural response is found at the first location, at least one of the second current levels being weighted by the nullity weighting information of method sub-action 1010, in which case method sub-action 1030 need not be executed.

Figure 3C:
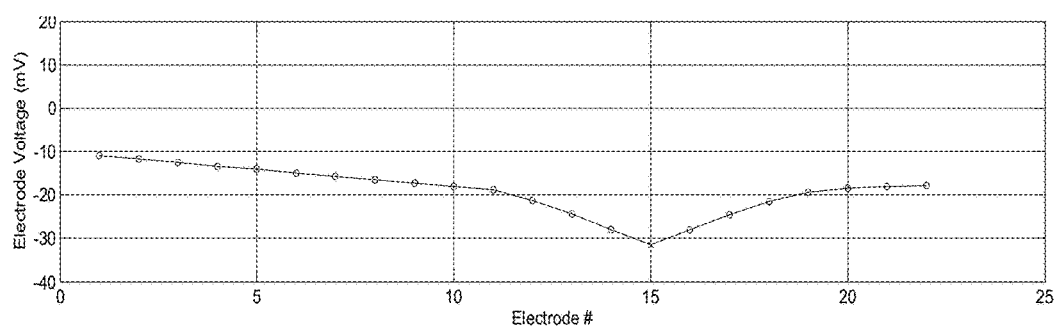
Figure 3D:
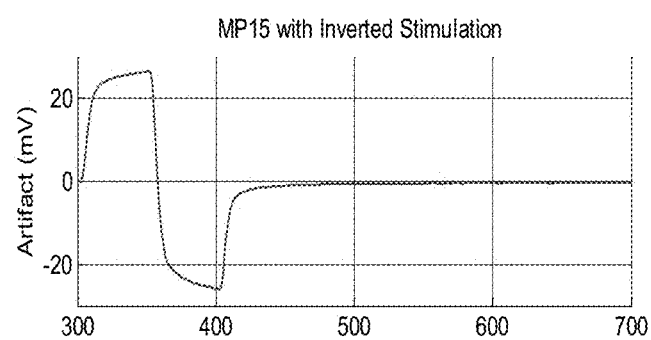

With respect to FIGS. 3B and 3C, an exemplary embodiment where current level is raised is that corresponding to a current level raised from 50 CL to 255 CL, which would result in an artefact about 64 times as large as that depicted in FIGS. 3B and 3C.

It is noted that method 1000 need not be executed such that the raising of the current level of the pertinent electrodes in method sub-action 1020 is raised by the same amount each time method sub-action 1020 is executed. Instead, the amount that can be raised each time sub-action 1020 is executed can be different.

In an alternate embodiment, there is a variation of method 1000 which can result in a more specific/precise determination of a threshold current level at which a neural response is detected, relative to that which is the case by executing method 1000 by only raising the current level of the electrodes. By way of example only and not by way of limitation, a variation of method 1000 can entail an iterative process in which the current levels are raised by a first factor each time method sub-action 1020 is executed. Upon a determination that the neural response is detected at method sub-action 1030, the current levels can be reduced by a second factor which is smaller than the first factor, and the current can be applied to the electrodes. If a neural response is detected, the current levels can be reduced by the second factor or a third factor which is smaller than the second factor. This iterative process can continue until a neural response is not detected, after which the current level of the pertinent electrodes can be raised by another factor which is smaller than the prior factors. By pursuing such an iterative method, a lower current level at which a neural response is detected can be determined as opposed to that which would be the case by executing method 1000 without such an iterative process. Any device, system, and/or method that can enable identification of threshold current levels that will result in the detection of a neural response can be utilized in at least some embodiments.

Figure 10B:
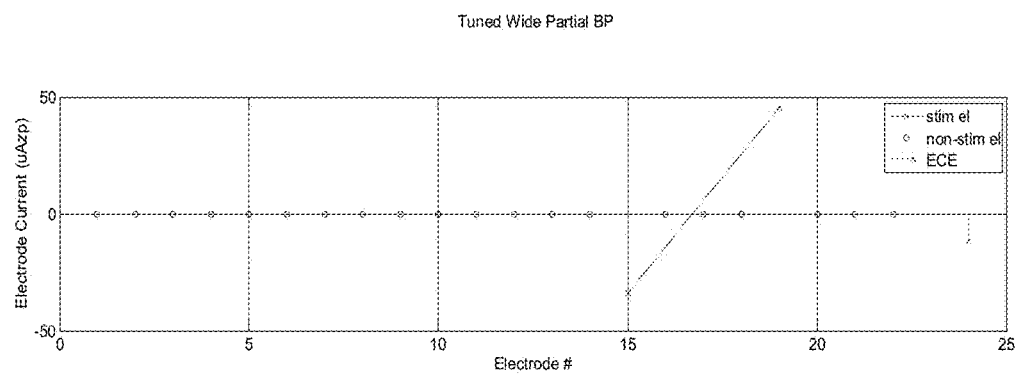
FIGS. 10B and 10C present exemplary graphics in support of descriptions of some exemplary embodiments.

It is noted that in at least some embodiments, method sub-actions 820, 940, 1020 and/or 1030 are executed utilizing tuned wide partial bipolar stimulation. FIG. 10B depicts an exemplary electrode current graph for current applied to a group of electrodes of an exemplary cochlear implant having an electrode array implanted into a cochlea of a recipient. The exemplary cochlear array has 22 intracochlear electrodes, corresponding to electrode #1-22 in FIG. 10B, and one extracochlear electrode (ECE) corresponding to electrode #24. It is noted that in alternate embodiments, there can be more or fewer electrodes implanted in the cochlea and/or than can be more or fewer extracochlear electrodes.

With respect to the graph presented in FIG. 10B, it can be seen that stimulation current is provided to an electrode group made up of intracochlear electrodes 19 and 15 of the exemplary electrode array and one extra cochlear electrode (ECE), all of which are part of the exemplary cochlear implant, and thus some of the current is returned via electrode 15 and some of the current is returned via the extra cochlear electrode, which can serve as a ground (although as noted above, in an alternate embodiment, at least some of the electrodes can be part of another component/another device which, in at least some embodiments is not implanted into the recipient and/or is inserted as a temporary matter into the recipient).

Figure 10C:
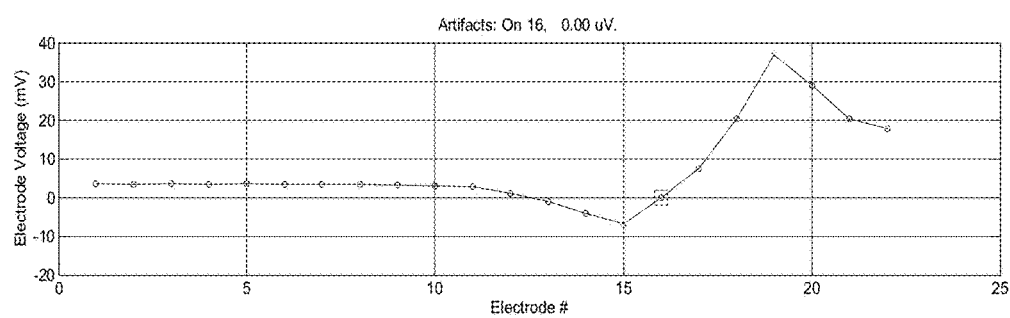

FIG. 10C depicts an exemplary voltage profile resulting from the stimulation corresponding to that presented in FIG. 10B. As can be seen, the tuned wide partial bipolar stimulation results in a voltage profile at and proximate to electrode 19 that is relatively similar to the voltage profile resulting from the monopolar stimulation presented in the graph of FIG. 3A above, but has a relatively sharp falloff towards lower number electrodes. Further, as can be seen there is a zeroed artefact at the first location corresponding to the recording electrode 16 of the electrode array of the cochlear implant. This is as compared to the voltage at that electrode presented in FIG. 3A above, which is above 20 mV. Accordingly, in an exemplary embodiment utilizing tuned wide partial bipolar stimulation in combination with the adjustment regimes detailed herein and/or variations thereof, an ECAP method can be executed such that there is substantially zero (including zero) artefact at the first location (recording location). Further, in an exemplary embodiment utilizing tuned wide partial bipolar stimulation in combination with the adjustment regimes detailed herein and/or variations thereof, an ECAP method can be executed such that there is a substantially reduced artefact at the first location relative to that which would be the case in the absence of utilizing the adjustment regimes detailed herein and/or variations thereof.

It is further noted that in at least some embodiments, method sub-actions 820, 940, 1020 and/or 1030 are executed utilizing tuned wide bipolar stimulation. In this regard, instead of utilizing the extracochlear electrode (ECE) as a return electrode, one or more of the intracochlear electrodes of the implanted electrode array are used as the return electrode(s). For example, continuing with the concept related to FIGS. 10B and 10C, current can be applied to electrode number 19 of the electrode array, and returned via, for example, electrode number 14 or 15. In an exemplary embodiment, such can result in a relatively small artefact/ substantially smaller artefact at the recording electrode relative to that which would be the case in the absence of utilizing the adjustment regimes detailed herein and/or variations thereof. It is noted that in at least some embodiments, the recording location (e.g., the recording electrode) might be different from that which is used when utilizing the exemplary wide partial bipolar stimulation. By way of example only and not by way of limitation in the aforementioned example where the return electrodes are electrodes 14 and/or 15, the recording electrode can be electrode 17 (as opposed to electrode 16 vis-à-vis the embodiments associated with FIGS. 10B and 10C). This is consistent with the teachings herein that entail that the adjustment regime can include adjusting the recording location. Continuing with the exemplary embodiment where electrodes 14 and 15 are the return electrodes, in the scenario where electrode 14 is the return electrode, there might be a slightly positive voltage recorded at the recording electrode 17, and in the scenario where electrode 15 is the return electrode, there might be a slightly negative voltage recorded at the recording electrode 17. In some embodiments, the adjustment regime is developed depending on whether or not a slightly positive voltage or slightly negative voltage is more utilitarian than the other with respect to the application of the teachings detailed herein and/or variations thereof. In some embodiments, it is the absolute value of the voltage at the recording electrode which is significant, and thus the return electrode is selected based on the lower absolute value of the voltage at the recording electrode, etc. In still other embodiments, the slightly positive voltage at the recording electrode and the separately recorded, slightly negative voltage at the recording electrode could be averaged in order to obtain an even smaller artefact.

In view of the above, it is clear that the teachings detailed herein and/or variations thereof include varying the electrodes of electrode groups that are used to provide stimulation and/or the recording electrode(s) to develop the adjustment regimes detailed herein. That is, in an exemplary embodiment, the adjustment regime entails adjusting the distance between one or more of the electrodes of the electrode group providing stimulation relative to the recording electrode. Any device, system, and/or method that can enable the tuned wide bipolar and/or tuned wide partial bipolar stimulation to result in a smaller artefact (including no artefact) at the recording location relative to that which would be the case in the absence of the adjustment regime can be utilized in at least some embodiments of the adjustment regimes detailed herein and/or variations thereof.

Figure 11:
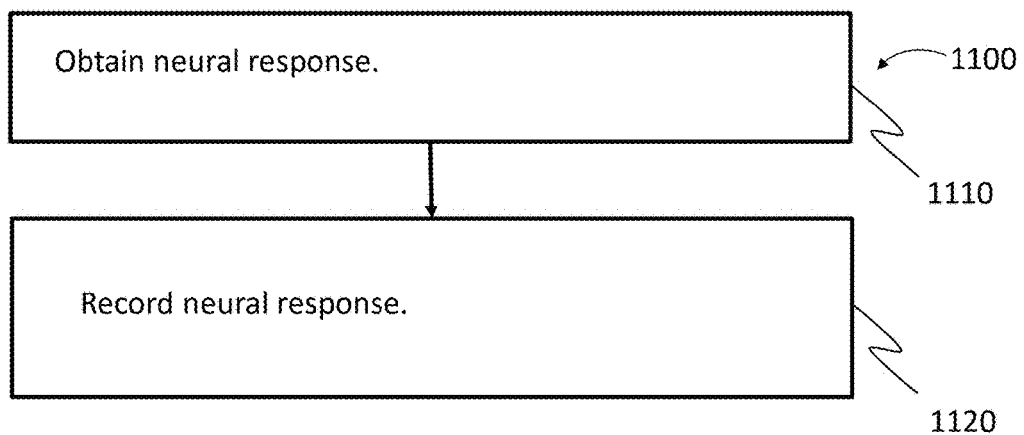
FIGS. 11 and 12 present exemplary flowcharts for exemplary algorithms according to exemplary embodiments.

FIG. 11 depicts an exemplary flowchart representing method 1100, which includes method sub-actions 1110 and 1120. Method sub-action 1110 entails executing method 1000. Method sub-action 1120 entails recording the neural response obtained in method sub-action 1110. Method sub-action 1120 can be executed using traditional ECAP recording technologies, or any other technology that can enable the teachings detailed herein and/or variations thereof to be practiced.

It is noted that in at least some embodiments, the action of recording a neural response can be executed via a cochlear implant or via another type of implant, such as by way of example only and not by way of limitation, an auditory brain stimulator, or the pertinent portions of a pacemaker, etc. In this vein, embodiments can include recording a neural response anywhere in (or outside of, if utilitarian) a recipient provided that the teachings detailed herein and/or variations thereof can be executed. Thus, the neural response can be recorded inside the cochlea and/or at another location (inside the brain and/or on the brain and/or outside the brain, on and/or in skin of a recipient etc.).

Figure 12:
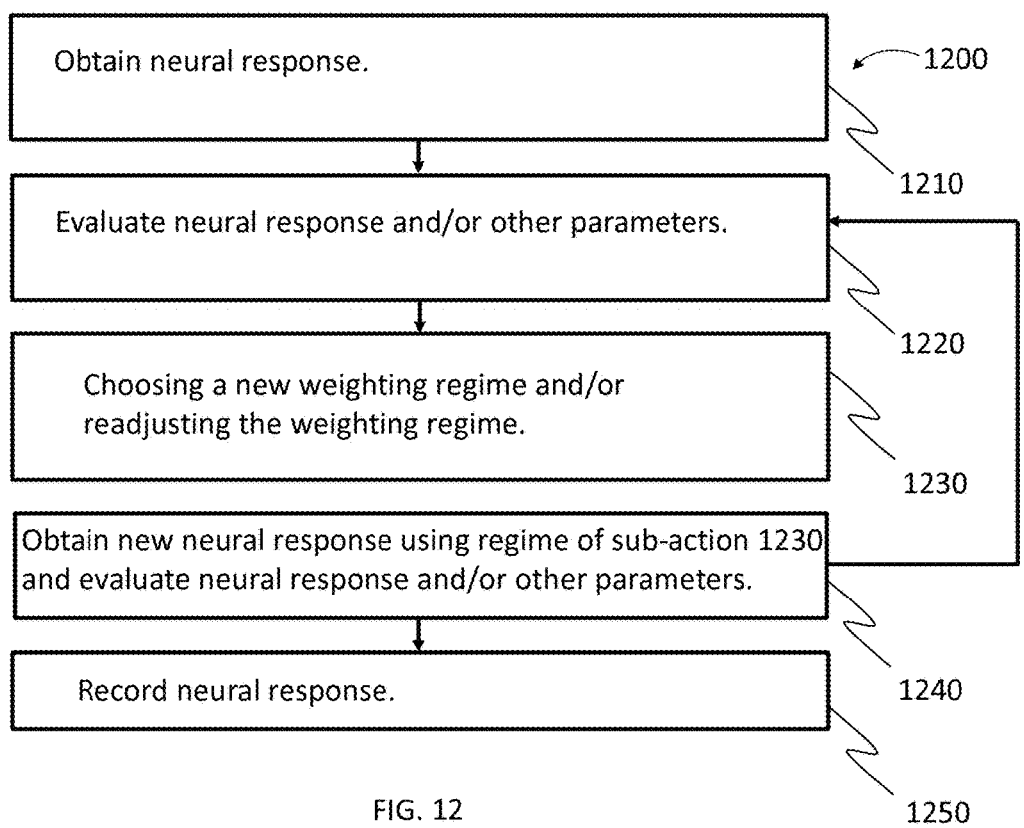
Figure 13:
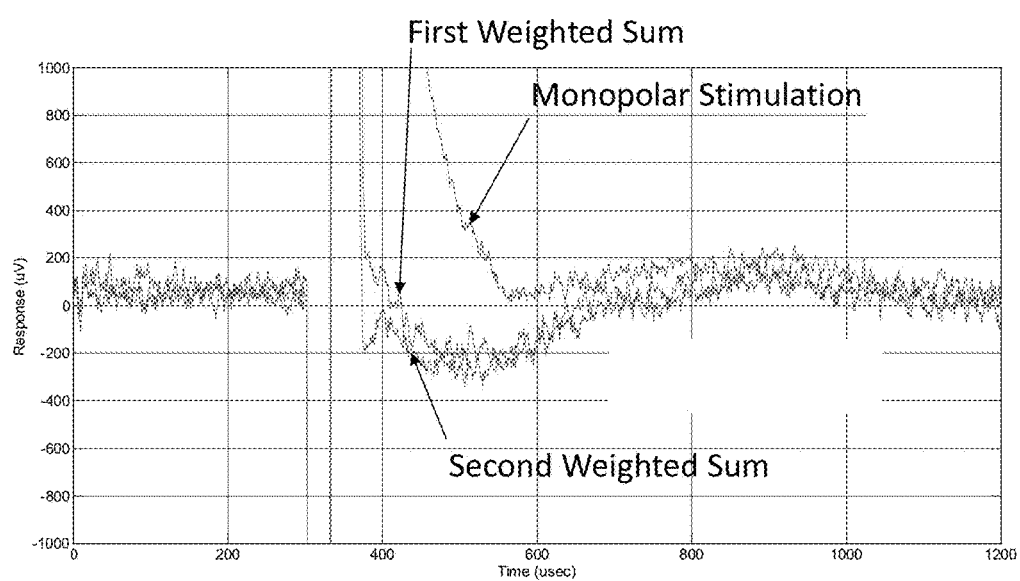
FIG. 13 presents an exemplary graphic in support of descriptions of some exemplary embodiments.

FIG. 12 depicts an exemplary flowchart representing method 1200, which can be executed as an alternate method to method 1100, or, more specifically, is a variation of method 1100, which entails compensating for noise and/or for non-linearities after the neural response is found by executing method sub-action 1110 of method 1100. As with method 1100, method 1200 includes the sub-action of obtaining a neural response (sub-action 1210) by executing method 1000. However, method 1200 includes method sub-action 1220, which entails evaluating the neural response and/or other parameters. Any parameters that can be evaluated that can determine the sufficiency of the neural response and/or other parameters vis-à-vis implementing the teachings detailed herein and/or variations thereof in a utilitarian manner can be utilized in at least some embodiments. Following method sub-action 1220, method sub-action 1230 is executed which entails choosing different weights/re-adjusting the weights to obtain a diminished artefact at the recording electrode relative to that which would be the case in the absence of the adjustment regime in general, and method sub-action 1220 in particular. In an exemplary embodiment, this can entail adjusting a current level difference between the pertinent electrodes. After sub-action 1230, sub-action 1240 is executed, which entails obtaining a new neural response utilizing the regime of sub-action 1230 and executing method action 1220 based on the new neural response. FIG. 13 depicts an exemplary chart of artefact responses at the recording electrode for monopolar stimulation, for tuned wide partial bipolar stimulation having a first weighted sum in current level amount, and for tuned wide partial bipolar stimulation having a second weighted sum in current level amount different from that of the first difference. In this regard, in an exemplary embodiment of the method 1200, the results of the recordings for the different weighting regimes used in method 1200 and the more utilitarian weighting regime can be selected based on a comparison of the results. Method 1200 further includes method action 1250 which entails recording the neural response as was the case in method 1120 of method 1100.

In at least some exemplary embodiments, method 1100 (including the various sub-actions that are part of method 1100 as detailed herein and/or variations thereof) is executed without NRT masking, and the recorded neural response has effectively the same pattern of changes in NRT magnitude as a function of level as in a NRT monopolar masking technique. Alternatively and/or in addition to this, method 1100 (including the various sub-actions that are part of method 1100 as detailed herein and/or variations thereof) is executed without NRT masking, and the recorded neural response has effectively the same absolute value N1-P1 magnitude as in a NRT monopolar masking technique.

Figure 14:
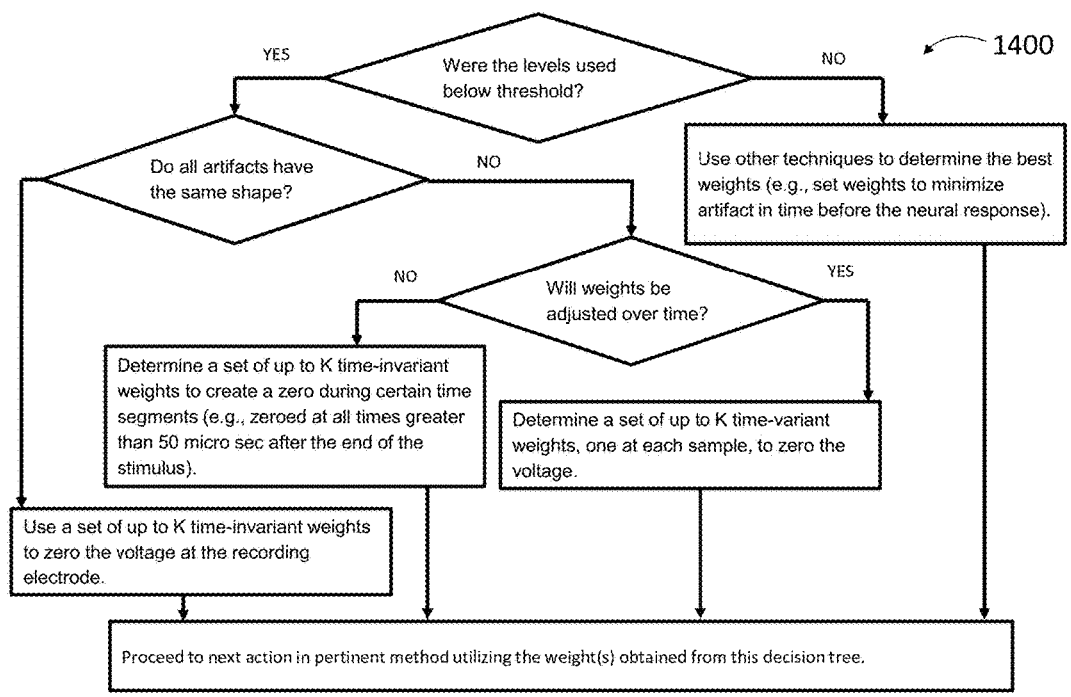
FIG. 14 presents an exemplary flowchart for an exemplary algorithm according to an exemplary embodiment.

Referring back to FIG. 6A, an exemplary alternate embodiment of method 220 will now be described. More particularly, method sub-action 224 of method 220 can correspond to that of the exemplary sub-method as detailed in FIG. 14. Sub-method 1400 includes the decision tree depicted therein, which will result in weight(s) that are used for actions subsequent to method action 224. In particular, sub-method 1400 is initially keyed upon the evaluation of whether the stimulation levels used to execute sub-action 222 of method 220 were sub-threshold (so there was no neural response). If not, the method entails using other techniques to determine utilitarian (e.g., best) weights (e.g., set weights to minimize artefact in time before the neural response, etc.), at least if the component recordings contain a neural response. Accordingly, an exemplary embodiment includes utilizing current levels that are above a threshold and/or contain neural response. That said, the decision tree of method 1400 further entails, if the levels were below the threshold and/or no neural response was present or otherwise detected, evaluating whether (i) all of the voltage artefacts on the recording electrodes are exactly the same shape. If so, and the weights will not be adjusted over time, method 1400 entails using a set of up to K time-invariant weights to zero (or substantially reduce) the artefact voltage at the recording electrode. If the artefacts have non-identical shapes as a function of time, a set of up to K time-variant weights, one at each sample (or less), can be is determined, to zero the voltage. If the weights will not be adjusted over time, a set of up to K time-invariant weights is determined to create a zero during certain time segments (e.g., zeroed at all times greater than 50 microseconds after the end of the stimulus).

As noted above, such an exemplary embodiment can be implemented by stimulating intracochlear electrodes 19 and 15 while recording on intracochlear electrodes 16. In an exemplary embodiment, this is performed so as to produce a similar voltage pattern as monopolar electrode stimulation to evoke a substantial neural response. In an exemplary embodiment, an artefact is recorded for a first electrode (e.g., electrode 19). The resulting voltage at electrode 16 is recorded. Subsequently, an artefact is recorded for electrode 15 at an inverted phase. Again the resulting voltage at electrode 16 is recorded A "Delta CL" is calculated, which is the difference in level between the current applied to electrode 19 and the current applied to electrode 15 that allows the artefact to recover to "zero" as rapidly as possible on recording electrode 16. This can be considered the sweet spot between over-shoot and under-shoot. If "Delta CL" is not zero, some current will flow to the monopolar return as well as the two intra-cochlear electrodes.

Next, the current level on electrode 19 is raised while keeping Delta CL constant. In at least some instances, there should not need to be adjustment and neural response will be observable in a probe-alone configuration. Alternatively, the components can be adjusted if utilitarianly viable. This is followed by finding a neural response by adjusting the current level of electrode 19, again while keeping Delta CL constant.

In an optional exemplary embodiment, confirmation can be achieved by f masking with a masker identical in form to probe (but xCL higher, where x=10 if that increase is observed to not be relatively too loud). The removal of the neural response can be confirmation that it is a neural effect.

In at least some embodiments, the goal is to reduce the artefact voltage at the recording electrode during the neural response. Accordingly, in at least some embodiments, any combination of artefacts from various stimulation electrodes can be utilized in order to reduce the overall artefact at the recording site, providing that the teachings detailed herein and/or variations thereof can be implemented. In an exemplary embodiment, wide partial bipolar (e.g., e1 19 vs. e115 & ECE1) is utilized with a Delta CL setting; recording on e1 16, which is used to produce a stimulation similar to monopolar stimulation. Partial TP can be used with return fraction tuned to produce zero artefact at the recording electrode. Psuedoinverses can be used to solve for weights that produce desired N voltages. Weighted pseudoinverses can be used to set specific voltages to desired levels (while putting less weight on the voltages on other electrodes). For example, weighted psuedoinverses are used to reduce voltage on recording electrode; alternatively and/or in addition to this, weighted psuedoinverses are used to determine weights both to reduce voltage on recording electrode and maintain a desired voltage profile (e.g., similar to monopolar or tripolar or Phased-Array). Probe and simultaneous nuller stimulus are used to produce zero artefact voltage on the recording electrode. (For example, probe and nullers are used with modes PA_noX where noX means the Phased-Array (PA) solution skips the given X electrode(s). Where X can be a single electrode or a set of electrodes (such as all odd electrodes in PA_even). PA_noY can be a similarly defined different set. Any stimulus can be used to produce the probe (TP, PA_even, PA_odd, PA_noX) and use a nuller stimulus (e.g., PA_noY) to produce zero voltage at recording electrode.

Next, Phased Array Compensation Factor (PACF) adjustments of a single probe stimulus can be used to produce zero voltage on a desired electrode. If for some reasons (perhaps due to quantization levels of current) exact cancellation of the artefact cannot be achieved, then artefact reduction can be attempted to reduce non-linearities of recording (and therefore allow other techniques such as template subtraction or alternating positive and negative recordings) to function better. Two stimuli can be set, one which has a transient over-shoot and another which has an under-shoot. These over and under shoots can be between the end of the stimulus and the beginning of the neural response and can have minimal change to the stimulation. Alternating between them and taking their sum can produce an artefact that cancels quickly after the stimulation is finished. Any method to combine artefacts in order to reduce the artefact at the recording electrode(s) can be utilized. One current source and wide bipolar mode can be used and the distance between the electrode pair (and the recording electrode) can be adjusted to get the desired, reduction in artefact voltage.

In view of the above, at least some embodiments reduce the large artefact that results from standard stimulation methods. In an exemplary embodiment, the teachings detailed herein and/or variations thereof are usable with ECAP signals of interest below 500 uV.

In at least some embodiments of the teachings detailed herein and/or variations thereof, implementation thereof reduces the artefact at the recording electrode towards zero, and can theoretically be zero (an infinite dB reduction). Some embodiments (such as the wide partial bipolar) can approach monopolar stimulation with respect to the thresholds and spread of excitation. Thus, at least some embodiments provide a response comparable to the relatively large magnitude neural response found with monopolar stimulation.

It is noted that while the embodiments detailed above are generally directed towards reducing stimulation artefact by nulling, other embodiments are directed towards the broader concept of influencing stimulation artefact utilizing the teachings detailed herein and/or variations thereof. That is, at least some embodiments include executing the teachings detailed herein and/or variations thereof in a manner does not necessarily result in the reduction of the artefact, but instead results in an influence on the artefact relative to that which would be the case in the absence of the various teachings detailed herein and/or variations thereof.

It is noted that at least some embodiments include any device, system and/or method that can enable the teachings detailed herein and/or variations thereof to be practiced. It is further noted that any method detailed herein corresponds to a disclosure of an apparatus and/or system configured to execute one or more or all of the method actions detailed herein and/or variations thereof. Such apparatuses and/or systems can utilize microprocessors, personal computers, customized computers, programmed and/or programmable devices having central processing units configured to automatically execute one or more or all of the method actions detailed herein and/or variations thereof. It is further noted that any device and/or system detailed herein corresponds to a disclosure of a method entailing operation of that device and/or a method entailing the actions that the device executes during operation thereof.

Figure 15:
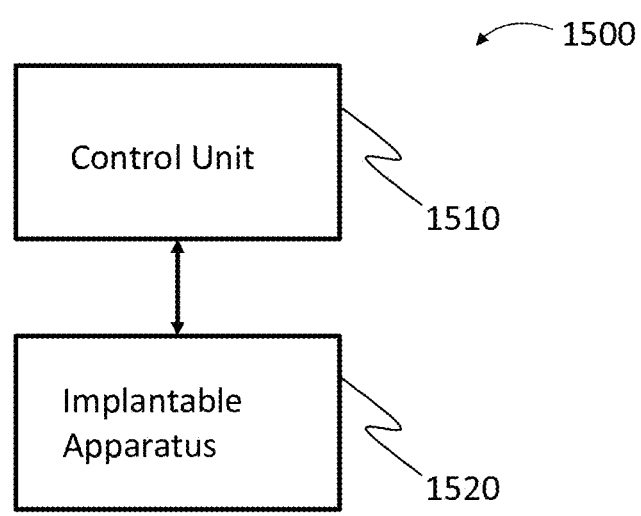
FIGS. 15-17 present exemplary systems according to some exemplary embodiments.

In this vein, referring to FIG. 15, an exemplary embodiment includes a system 1500. The system includes a control unit 1510 an implantable apparatus 1520 including a plurality of electrodes 1520. In an exemplary embodiment, the control unit 1510 can be a processor (e.g., a microprocessor) having programming therein (software and/or firmware) and/or circuitry arranged to control the implantable apparatus as will now be detailed.

In an exemplary embodiment, the implantable apparatus 1520 corresponds to any of the devices and/or systems detailed herein (e.g., the implantable component(s) of the cochlear implant 100, the electrode array 146, etc.). In an exemplary embodiment, the control unit can correspond to the control components of the cochlear implant 100, whether they be in the external component 142 or in the implantable component(s). In an exemplary embodiment, the control unit can be a separate component from the prosthesis. In an exemplary embodiment, the control unit can be apart of an implantable assembly, in which case both the control unit 1510 and the implantable apparatus are part of an implantable assembly. In an exemplary embodiment, the control unit can be a component of a fitting system for a tissue stimulating prosthesis (e.g., a cochlear implant), such as a computer (e.g., a personal computer customized for executing one or more or all of the method actions herein and/or for controlling other components to execute one or more or all of the method actions detailed herein.

Accordingly, in an exemplary embodiment, the system is configured to execute one or more or all of the method actions detailed herein. In an exemplary embodiment, such is performed automatically upon a command inputted by a user (audiologist or recipient, etc.).

In an exemplary embodiment, the implantable apparatus 1520 is configured to apply, in a controlled manner under the control of the control unit 1510, respective first electrical currents to the respective electrodes of the plurality of electrodes such that respective stimulating electrical currents emanate from the respective electrodes of the plurality of electrodes. The system 1500 is configured to obtain respective information on respective artifact voltages at a first location resulting from the respective stimulations. The implantable apparatus 1520 is configured to apply, subsequent to the application of the first electrical currents, in a controlled manner under the control of the control unit, respective second electrical currents to the respective electrodes of the plurality of electrodes such that respective stimulating electrical currents emanate from the respective electrodes of the plurality of electrodes and such that the stimulation artifact at the first location is substantially about zero.

Figure 16:
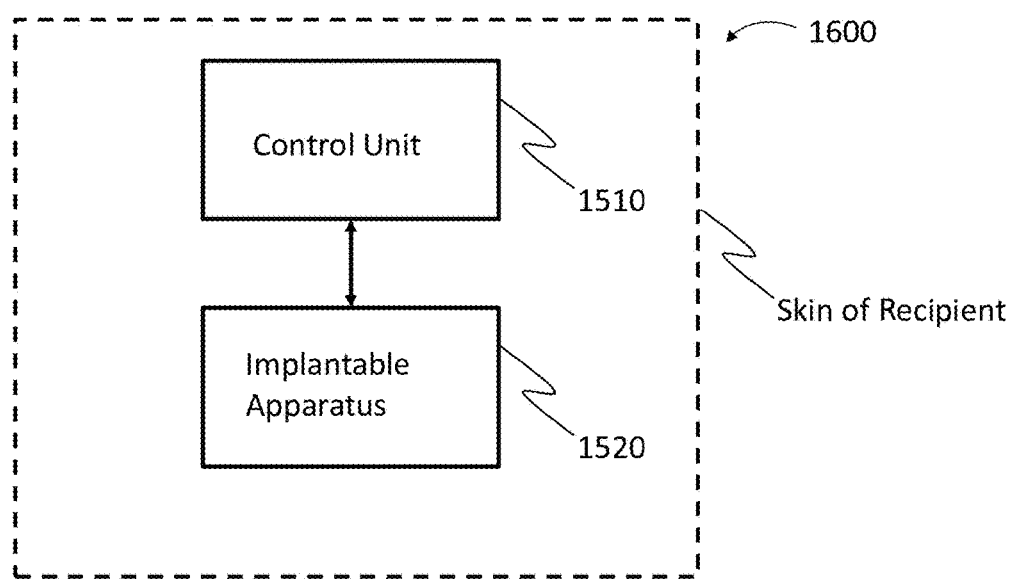
Figure 17:
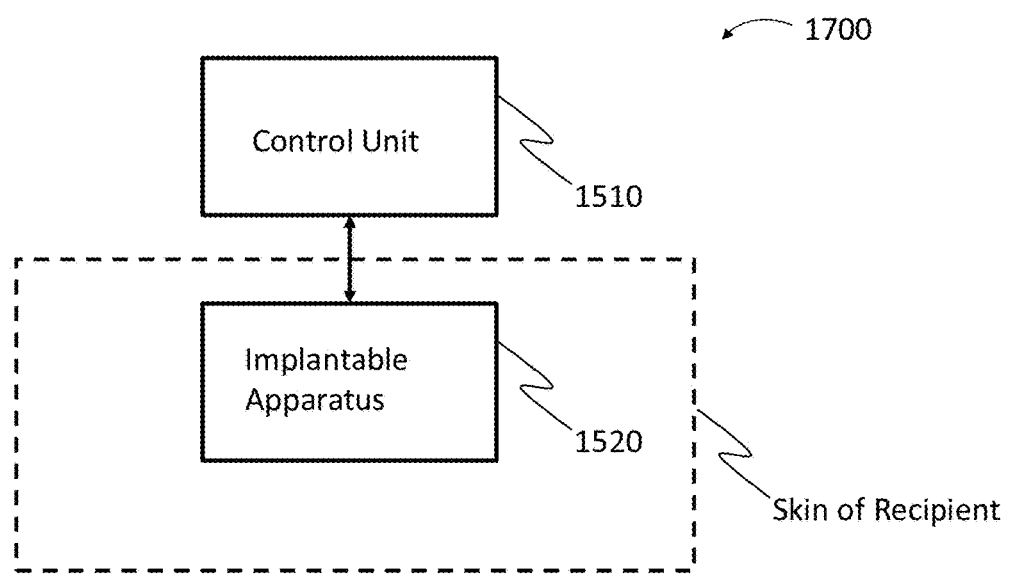

Referring now to FIG. 16, there is a system 1600 that corresponds to system 1500, where the control unit 1510 and the implantable apparatus 1520 are implantable in a recipient, as evidenced by the dashed lines about system 1500. Conversely, referring now to FIG. 17, there is a system 1700 that corresponds to system 1500, where the control unit 1510 is an external component and the implantable apparatus 1520 is implantable in a recipient.

In an exemplary embodiment, there is a non-transitory computer readable medium having recorded thereon, a computer program for executing one or more or all of the method actions detailed herein. For example, in an exemplary embodiment, there is a non-transitory computer readable medium having recorded thereon, a computer program for executing a method, program including code for supplying a first electrical current to at least a first electrode implanted in a cochlea of a recipient such that a first stimulating electrical current emanating from the first electrode stimulates the cochlea of the recipient, code for obtaining a property of an electrical voltage resulting from the first stimulating electrical current at at least one recording electrode that is implanted in the recipient at an intracochlear location, code for supplying a second electrical current to at least a second electrode implanted in the recipient cochlea such that a second stimulating electrical current emanating from the second electrode stimulates the cochlea of the recipient, code for obtaining a property of an electrical voltage resulting from the second electrical current at the at least one recording electrode, and code for determining, based on the obtained properties, at least one weighting that when at least one of the first and second electrical currents is adjusted thereby would result in a summation of the voltages of the first stimulating electrical current and the second stimulating electrical current at the at least one recording electrode to be closer to zero than that which would be the case in the absence of the weighting.

While various embodiments of the present invention have been described above, it should be understood that they have been presented by way of example only, and not limitation. It will be apparent to persons skilled in the relevant art that various changes in form and detail can be made therein without departing from the spirit and scope of the invention.

What is claimed is:

1. A method, comprising:
reducing a stimulation artefact of an implantable stimulator including a plurality of stimulating electrodes by:
obtaining respective information on respective artefact voltages at a first location resulting from stimulation by one electrode group or respective electrode groups of the implanted stimulator; and
determining an adjustment regime based on the obtained information that results in a reduction of the stimulation artefact at the first location relative to that which would be the case in the absence of the regime,
wherein the action of obtaining respective information on respective artefact voltages at the first location includes:
supplying a first electrical current to at least a first electrode implanted in a recipient such that a first stimulating electrical current emanating from the first electrode stimulates tissue of the recipient;
obtaining a property of an electrical voltage resulting from the first stimulating electrical current at at least one recording electrode that is implanted in the recipient at the first location;
supplying a second electrical current to at least a second electrode implanted in the recipient such that a second stimulating electrical current emanating from the second electrode stimulates tissue of the recipient; and
obtaining a property of an electrical voltage resulting from the second stimulating electrical current at the at least one recording electrode.

2. The method of claim 1, wherein:
the implanted stimulator is a cochlear implant.

3. The method of claim 2, wherein:
the respective artefacts at the first location result from stimulation by one electrode group of the stimulator; and
the one electrode group comprises only intracochlear electrodes.

4. The method of claim 3, wherein the one electrode group comprises only two electrodes.

5. The method of claim 2, wherein:
the respective artefacts at the first location result from stimulation by one electrode group of the stimulator; and
the one electrode group comprises an intracochlear electrode and an extracochlear electrode.

6. The method of claim 1, wherein:
the regime is at least one of an electrode activation regime or a first location adjustment regime or a current adjustment regime.

7. The method of claim 1, wherein:
the regime is a weighting regime.

8. The method of claim 7, wherein:
the regime is a current weighting regime.

9. The method of claim 1, wherein:
the respective information is obtained at respective different temporal periods.

10. The method of claim 1, wherein:
the respective artefacts at the first location result from stimulation by respective electrode groups of the stimulator; and
one of the electrode groups of the respective electrode groups includes a stimulating electrode that is different from the stimulating electrodes of another of the respective electrode groups.

11. The method of claim 1, wherein:
the first location is a location corresponding to a separate apparatus from the implanted stimulator.

12. The method of claim 1, wherein:
the regime is an electrode activation regime.

13. The method of claim 1, wherein:
the regime is a first location adjustment regime.

14. The method of claim 1, wherein:
the regime is a current adjustment regime.

15. The method of claim 1, wherein the action of determining an adjustment regime includes:
determining, based on the obtained respective information, at least one weighting that when at least one of a first and a second electrical current to be applied to respective electrodes of the electrode group or groups is adjusted thereby would result in a summation of voltages of a first stimulating electrical current and a second stimulating electrical current at the first location to be closer to zero than that which would be the case in the absence of the weighting.

16. The method of claim 1, wherein the action of determining an adjustment regime includes:
determining, based on the obtained properties, at least one weighting that when at least one of the first and second electrical currents is adjusted thereby would result in a summation of the voltages of the first stimulating electrical current and the second stimulating electrical current at the at least one recording electrode to be closer to zero than that which would be the case in the absence of the weighting.

17. The method of claim 1, wherein the action of determining an adjustment regime includes:
determining at least one weighting that when at least one of a first and second electrical currents applied by an electrode of the one electrode group or respective electrode groups of the implanted stimulator is adjusted thereby would result in a summation of voltages of a first stimulating electrical current and a second stimulating electrical current at the at the at least one electrode to be substantially zero.

18. The method of claim 1, wherein the first electrode is part of a first electrode group of the implanted stimulator and the second electrode is part of a second electrode group of the implanted stimulator.

19. A system comprising:
a control unit; and
an implantable apparatus including a plurality of electrodes, wherein
the implantable apparatus is configured to apply, in a controlled manner under the control of the control unit, respective first electrical currents to the respective electrodes of the plurality of electrodes such that respective stimulating electrical currents emanate from the respective electrodes of the plurality of electrodes,
the system is configured to obtain respective information on respective artifact voltages at a first location resulting from the respective stimulations,
the application of respective first electrical currents to the respective electrodes corresponds to applying an electrical current to at least a first electrode of the respective electrodes such that a first stimulating electrical current emanates from the first electrode to stimulates tissue of the recipient, and the application of respective first electrical currents to the respective electrodes also corresponds to applying an electrical current to at least a second electrode of the respective electrodes such that a second stimulating electrical current emanates from the second electrode to stimulates tissue of the recipient;
the obtaining of respective information on respective artifact voltages at the first location resulting from the respective stimulations is executed by:
obtaining a first property of an electrical voltage resulting from the first stimulating electrical current at the at least one recording electrode at the first location; and
obtaining a second property of an electrical voltage resulting from the second stimulating electrical current at the at least one recording electrode at the first location.

20. The system of claim 19, wherein:
the control unit and the implantable apparatus are implantable in a recipient.

21. The system of claim 19, wherein:
the implantable apparatus are implantable in a recipient; and
the control unit is an external device.

22. The system of claim 19, wherein:
the implantable apparatus are implantable in a recipient; and
the control unit is part of a fitting system.

23. The system of claim 19, wherein:
the implantable apparatus is configured to apply, subsequent to the application of the first electrical currents, in a controlled manner under the control of the control unit, respective second electrical currents to the respective electrodes of the plurality of electrodes such that respective stimulating electrical currents emanate from the respective electrodes of the plurality of electrodes and such that the stimulation artifact at the first location is substantially about zero.

24. The system of claim 19, wherein:
the implantable apparatus is configured to apply, based on the obtained respective information, subsequent to the application of the first electrical currents, in a controlled manner under the control of the control unit, respective second electrical currents to the respective electrodes of the plurality of electrodes such that respective stimulating electrical currents emanate from the respective electrodes of the plurality of electrodes and such that the stimulation artifact at the first location is substantially about zero.

25. The system of claim 19, wherein:
the implantable apparatus is configured to use the obtained respective information on respective artifact voltages at the first location to adjust an operation of the implantable apparatus such that subsequent application of electrical currents results in effectively no stimulation artifact at the first location.

* * * * *